US012628889B2

(12) United States Patent
Jayaraman et al.

(10) Patent No.: US 12,628,889 B2
(45) Date of Patent: May 19, 2026

(54) CUSTOM-FIT REUSABLE RESPIRATORY PROTECTIVE DEVICE

(71) Applicant: Georgia Tech Research Corporation, Atlanta, GA (US)

(72) Inventors: Sundaresan Jayaraman, Atlanta, GA (US); Sungmee Park, Atlanta, GA (US)

(73) Assignee: Georgia Tech Research Corporation, Atlanta, GA (US)

( * ) Notice: Subject to any disclaimer, the term of this patent is extended or adjusted under 35 U.S.C. 154(b) by 301 days.

(21) Appl. No.: 18/162,315

(22) Filed: Jan. 31, 2023

(65) Prior Publication Data

US 2023/0284715 A1 Sep. 14, 2023

Related U.S. Application Data

(60) Provisional application No. 63/304,893, filed on Jan. 31, 2022.

(51) Int. Cl.
| | |
|---|---|
| *A41D 13/11* | (2006.01) |
| *A62B 18/02* | (2006.01) |
| *A62B 18/08* | (2006.01) |
| *A62B 27/00* | (2006.01) |

(52) U.S. Cl.
CPC ...... *A41D 13/1161* (2013.01); *A41D 13/1107* (2013.01); *A41D 13/1153* (2013.01); *A62B 18/02* (2013.01); *A62B 18/08* (2013.01); *A62B 27/00* (2013.01); *A61M 2207/10* (2013.01)

(58) Field of Classification Search
CPC .. A41D 13/11–1192; A62B 18/02–025; A62B 18/08; A62B 18/084; A62B 23/00–04; A62B 27/00; A62B 18/00; A61M 2207/00; A61M 2207/10
See application file for complete search history.

(56) References Cited

U.S. PATENT DOCUMENTS

| | | | |
|---|---|---|---|
| 1,942,442 | A | 1/1934 | Motsinger |
| 2,176,709 | A | 10/1939 | Dym |
| 3,013,556 | A | 12/1961 | Galleher, Jr. |

(Continued)

OTHER PUBLICATIONS

Institute of Medicine. 2008. Preparing for an Influenza Pandemic: Personal Protective Equipment for Healthcare Workers. Washington, DC, https://doi.org/10.17226/11980.

(Continued)

*Primary Examiner* — Michelle J Lee
(74) *Attorney, Agent, or Firm* — Meunier Carlin & Curfman LLC

(57) ABSTRACT

An exemplary apparatus and method are disclosed for a respiratory protective device. The respiratory protective device can be customized to the facial profile of a user and ensure proper fit and operation of device and attached breathable filter. In some embodiments, the device is configured to continuously monitor, via an integrated sensor embedded in the device's frame, the fit or proper particulate-filtering operation of the respiratory protective device. The sensor embodiment can ensure proper operation of respiratory protective device while providing monitoring and tracking of the fit to ensure personal safety for the healthcare professionals wearing the device.

8 Claims, 30 Drawing Sheets

(56)  References Cited

U.S. PATENT DOCUMENTS

| | | | | |
|---|---|---|---|---|
| 3,040,741 A * | 6/1962 | Carolan | ............... | A62B 18/084 |
| | | | | 128/207.11 |
| 6,701,925 B1 * | 3/2004 | Resnick | ................. | A62B 17/04 |
| | | | | 128/205.27 |
| 8,573,199 B2 | 11/2013 | King et al. | | |
| 10,646,731 B2 | 5/2020 | Jayaraman et al. | | |
| 10,646,732 B2 | 5/2020 | Rachapudi et al. | | |
| 10,843,015 B2 | 11/2020 | Patil et al. | | |
| 11,484,734 B2 | 11/2022 | Waterford et al. | | |
| 11,969,035 B2 | 4/2024 | Qu et al. | | |
| 2011/0197341 A1 | 8/2011 | Formica et al. | | |
| 2012/0042878 A1 | 2/2012 | Woo | | |
| 2015/0040910 A1 * | 2/2015 | Koehler | ............... | A62B 18/082 |
| | | | | 128/205.27 |
| 2015/0157822 A1 | 6/2015 | Karpas et al. | | |
| 2016/0354571 A1 | 12/2016 | Grashow | | |
| 2017/0173371 A1 * | 6/2017 | Truex | ..................... | A62B 18/02 |
| 2017/0361045 A1 | 12/2017 | Fu et al. | | |
| 2019/0134436 A1 | 5/2019 | Thompson et al. | | |
| 2020/0114178 A1 * | 4/2020 | Waterford | ............ | A62B 23/025 |
| 2021/0322796 A1 | 10/2021 | Hubbard et al. | | |
| 2021/0361003 A1 | 11/2021 | Barr | | |
| 2021/0402222 A1 | 12/2021 | Kwon et al. | | |
| 2022/0024139 A1 * | 1/2022 | Schwartz | ............... | A62B 18/02 |
| 2022/0105369 A1 | 4/2022 | Lee | | |
| 2023/0047226 A1 | 2/2023 | Van Zanten et al. | | |
| 2023/0149647 A1 * | 5/2023 | Evans | ..................... | A62B 18/08 |
| | | | | 128/206.24 |
| 2023/0284714 A1 * | 9/2023 | Chahine | ................. | A41D 13/11 |

OTHER PUBLICATIONS

Institute of Medicine. 2006. Reusability of Facemasks During an Influenza Pandemic: Facing the Flu. Washington, DC, https://doi.org/10.17226/11637. Read free on-line: https://nap.nationalacademies.org/read/11637/chapter/1.

National Academies of Sciences, Engineering, and Medicine. 2019. Reusable Elastomeric Respirators in Health Care: Considerations for Routine and Surge Use. Washington, DC: The National Academies Press. https://doi.org/10.17226/25275. Read free on-line: https://nap.nationalacademies.org/read/25275/chapter/1.

Roberge, R., Niezgoda, G., Benson, S., Analysis of Forces Generated by N95 Filtering Facepiece Respirator Tethering Devices: A Pilot Study, Journal of Occupational and Environmental Hygiene, 9 (8), 2012, pp. 527-533.

Zhuang, Z., Bergman, M., Lei, Z., Niezgoda, G. & Shaffer, R. (2017) Recommended test methods and pass/fail criteria for a respirator fit capability test of half-mask air-purifying respirators. J. Occup. Environ. Hyg. 14, 473-481. https://doi.org/10.1080/15459624.2017.1296233.

Yang J, Dai J, Zhuang Z. Simulating the interaction between a respirator and a headform using LS-DYNA. Computer-Aided Design Appl. 2009; 6(4):539-551.

Protecting facial skin under N95 face masks, National Pressure Injury Advisory Panel, https://cdn.ymaws.com/npiap.com/resource/resmgr/position_statements/NPIAP_-Mask_Injury_Infograp.pdf, Last Accessed: Jun. 19, 2020.

Lam, U-Nee., Siddik, Nur., Yussof, Shah., and Ibrahim, S. (2020) N95 respirator associated pressure ulcer amongst COVID-19 health care workers, Int Wound J. Oct. 17(5): 1525-1527, doi: 10.1111/iwj.13398.

Oot-Giromini B, Bidwell FC, Heller NB, et al. Pressure ulcer prevention versus treatment, comparative product cost study. Decubitus 1989; 2(3):52-4.

Cleaning and Disinfecting 3M Reusable Elastomeric Half and Full Facepiece Respirators following Potential Exposure to Coronaviruses, https://multimedia.3m.com/mws/media/17939590/cleaning-and-disinfecting-3m-reusable-respirators-following-potential-exposure-to-coronaviruses.pdf.

Cai, M., Li., H., Shen, S., Wang, Y, and Yang, Q. (2018) "Customized design and 3D printing of face seal for an N95 filtering facepiece respirator", Journal of Occupational and Environmental Hygiene, 15:3, 226-234, https://doi.org/10.1080/15459624.2017.1411598.

Zhuang, Z., & Bradtmiller, B. (2005) A Head-and-Face Anthropometric Survey of U.S. Respirator Users. J Occup Environ Hyg. Nov; 2 (11):567-76. DOI: https://10.1080/15459620500324727. PMID: 16223715.

3dMD. (2020) Retrieved from https://3dmd.com/products/.

Granta. (2020) Chart from CES EduPack, ANSYS Granta. 2019.

Ashby. (2008) The CES EduPack Database of Natural and Man-Made Materials, Version 1.0, Granta Design, Cambridge, UK, Jan. 2008.

Shore. (2020) "Shore hardness scale," https://www.smooth-on.com/page/durometer-shore-hardness-scale/, Last Accessed: Nov. 14, 2020.

Formlabs. (2022a) Elastic 50A, https://formlabs.com/materials/flexible-elastic/. Last Accessed: Jun. 19, 2022.

Carbon 3D. (2022) SIL 30, https://www.carbon3d.com/materials/sil-30, Last Accessed: Jun. 18, 2022.

Dow. (2022) Silastic™ 3D 3335 Liquid Silicone Rubber, https://www.dow.com/en-us/pdp.silastic-3-d-3335-liquid-silicone-rubber-1sr.4137603z.html?productCatalogFlag=1#overview, Last Accessed: Jun. 18, 2022

Elkem. (2019) Silicones 3D Flyer Industrial, https://www.elkem.com/silicones/brands/amsil/, Last Accessed: Jun. 18, 2022.

Chopra, J., Abiakam, N., and Kim, H. (2021) The influence of gender and ethnicity on facemasks and respiratory protective equipment fit: a systematic review and meta-analysis. BMJ Global Health 6:e005537. doi: 10.1136/bmjgh-2021-005537.

Zhuang, Z., Groce, D., Ahlers, H. W., Iskander, W., Landsittel, D., Guffey, S., Benson, S., Viscusi, D., and Shaffer, R. E. (2008) Correlation between Respirator Fit and Respirator Fit Test Panel Cells by Respirator Size. Journal of Occupational and Environmental Hygiene, 5(10), 617-628. https://doi.org/10.1080/15459620802293810.

Lin, Y.C., & Chen, C.P. (2017) Characterization of small-to-medium head-and-face dimensions for developing respirator fit test panels and evaluating fit of filtering facepiece respirators with different faceseal design. PLOS ONE, 12(11), e0188638. https://doi.org/10.1371/journal.pone.0188638.

NASEM. (2022) Frameworks for Protecting Workers and the Public from Inhalation Hazards. Washington, DC: The National Academies Press. https://doi.org/10.17226/26372.

Contrera, J. (2020) "The N95 shortage America can't seem to fix", The Washington Post, Sep. 21, 2020.

Lam, S.C., Lee, J.K.L., Yau, S.Y., and Charm, C.Y.C. (2011) "Sensitivity and specificity of the user-seal-check in determining the fit of N95 respirators", Journal of Hospital Infection 77 252-256, DOI: https://doi.org/10.1016/j.jhin.2010.09.034.

Radonovich, L.J., Cheng, J., Shenal, BV., Hodgson, M., and Bender, BS. (2009) Respirator Tolerance in Health Care Workers. JAMA. 301(1):36-38. doi: 10.1001/jama.2008.894.

Cai M., et al., "Customized Design and 3D Printing of Face Seal for an N95 Filtering Facepiece Respirator," Journal of Occupational and Environmental Hygiene, 2018, vol. 15, No. 3, pp. 226-234 (26 Pages) Retrieved from URL: https://doi.org/10.1080/15459624.2017.1411598.

D'agostino S., "Voronoi Tessellations and Scutoids Are Everywhere," Scientific American, Jan. 22, 2019, pp. 1-7, Retrieved from URL: https:// blogs.scientificamerican.com/observations/voronoi-tessellations-and-scutoids-are-everywhere/.

ELKEM: "AMSil™, The brand for Silicones Tailored for Use by Additive Manufacturing Printing worldwide," Silicones 3D Flyer Industrial, 3 Pages, [Retrieved on Oct. 15, 2024] Retrieved from URL: https://www.elkem.com/silicones/brands/amsil/.

Lee W., et al., "A 3D Anthropometric Sizing Analysis System Based On North American Caesar 3D Scan Data For Design of Head Wearable Products," Computers & Industrial Engineering, Mar. 2018, vol. 117, pp. 121-130 (7 Pages).

National Academies: "Preparing for an Influenza Pandemic: Personal Protective Equipment for Healthcare Workers," Institute of Medicine, 2008, 11 pages, [Retrieved on Oct. 15, 2024] Retrieved

(56) References Cited

OTHER PUBLICATIONS from URL: https://map.nationalacademies.org/catalog/11980/preparing-for-an-influenza-pandemic-personal-protective-equipment-for-healthcare.

National Academies: "Reusable Elastomeric Respirators in Health Care: Considerations for Routine and Surge Use," National Academies of Sciences, Engineering, and Medicine, 2019, 10 Pages, [Retrieved on Oct. 15, 2024] Retrieved from URL: https://map.nationalacademies.org/catalog/25275/ruusable-elastomeric-respirators-in-health-care-considerations-for-routine-and.

Non-Final Office Action for U.S. Appl. No. 18/162,323 dated Sep. 8, 2025, 25 pages.

Non-Final Office Action for U.S. Appl. No. 18/162,323, mailed Sep. 8, 2025, 25 pages.

Notice of Allowance for U.S. Appl. No. 18/162,312, mailed Oct. 28, 2025, 8 pages.

Zhuang Z., et al., "Correlation Between Respirator Fit and Respirator Fit Test Panel Cells by Respirator Size," Journal of Occupational and Environmental Hygiene, Oct. 2008, vol. 5, No. 10, pp. 617-628 (13 Pages).

Zhuang Z., et al., "Head-and-Face Anthropometric Survey of U.S. Respirator Users," Journal of Occupational and Environmental Hygiene, PMID: 16223715, Nov. 2005, vol. 2, No. 11, pp. 567-576 (1 Page), Retrieved from URL: https://10.1080/15459620500324727.

Zhuang Z., et al., "Recommended Test Methods And Pass/Fail Criteria for a Respirator Fit Capability Test of Half-Mask Air-Purifying Respirators," Journal of Occupational and Environmental Hygiene, 2017, vol. 14, No. 6, pp. 473-481 (4 Pages) Retrieved from URL: https://doi.org/10.1080/15459624.2017.1296233.

Niosh, https://www.cdc.gov/niosh/hierarchy-of-controls/about/index.html.

Park, S., Tian, Y., Bergman, M., Pollard, J., Zhuang, Z., and Jayaraman, S., Next Generation Custom-Fit Reusable Respiratory Protective Device with Continuous Fit Monitoring—Part I: Custom-Fit Design, Journal of the International Society of Respiratory Protection, vol. 41, No. 1, 2024, 22-37.

Roberge R, Niezgoda G, and Benson S. (2012) Analysis of Forces Generated by N95 Filtering Facepiece Respirator Tethering Devices: A Pilot Study, Journal of Occupational and Environmental Hygiene, 9 (8), 527-533.

Yang J, Dai J, Zhuang Z. (2009) Simulating the interaction between a respirator and a headform using LS-DYNA. Computer-Aided Design Appl. 6(4):539-551.

Radonovich LJ, Cheng J, Shenal BV, Hodgson M, and Bender BS. (2009) Respirator Tolerance in Health Care Workers. Journal of the American Medical Association. 301(1):36-38. doi: 10.1001/jama.2008.894.

Lam SC, Lee JKL, Yau SY, and Charm CYC. (2011) Sensitivity and specificity of the user-seal-check in determining the fit of N95 respirators, Journal of Hospital Infection 77 252-256. https://doi.org/10.1016/j.jhin.2010.09.034.

Stokowski LA. (2020) A Step-by-Step Guide to Preventing PPE-Related Skin Damage. MedScape. Retrieved from https://www.medscape.com/viewarticle/929590.

National Pressure Injury Advisory Panel. (2020) https://cdn.ymaws.com/npiap.com/resource/resmgr/position_statements/NPIAP_-_Mask_Injury_Infograp.pdf.

Jayaraman, S., Next Generation Custom-Fit Reusable N95 Respirator with Fit Monitoring, Final Technical Report, Sj-TR-CDC-06-22. Jun. 30, 2022. 109 pages.

Park, S., Tian, Y., Bergman, M., Pollard, J., Zhuang, Z., and Jayaraman, S., Next Generation Custom-Fit Reusable Respiratory Protective Device with Continuous Fit Monitoring—Part II: Continuous Fit Monitoring, Journal of the International Society of Respiratory Protection, vol. 41, No. 1, Jul. 2024, pp. 38-56.

OSHA 1910.134 App A, Fit Testing Procedures (Mandatory), https://www.osha.gov/laws regs/regulations/standardnumber/1910/1910.134AppA.

Sungmee Park, et al., Next-Generation Custom-Fit Reusable Respiratory Protective Device with Continuous Fit Monitoring—Part III: 3D Printing of Prototypes and Evaluation. Journal of the International Society for Respiratory Protection, vol. 41, No. 2, 2024, 12 pages.

* cited by examiner 7.50 mm 5.50 mm 4.75 mm 2.25 mm 2.50 mm bottom
(B)

Ø = 6.00 mm 2.25 mm top
(A)

6.00 mm 5.00 mm 2.00 mm 11.00 mm

380a

382a

372

386 side
(C)

Helix pitch = 1.00 mm
Pipe diameter = 0.50 mm
Screw of 5 turns

370a

Chamfer = 1.00 mm

388

R = 0.25 mm

384 conforms to the Cover
Piece base surface

382a

380a

372

386

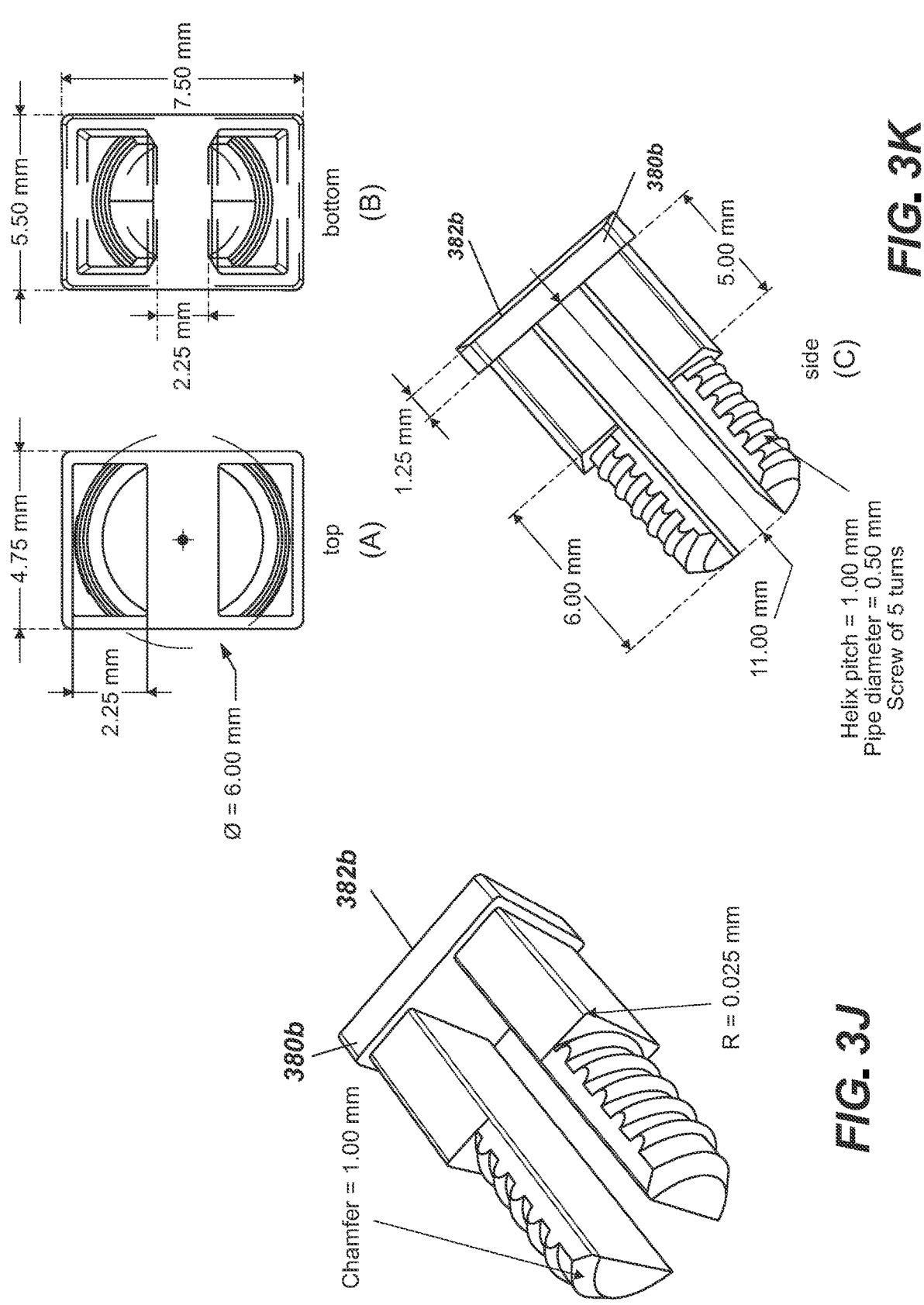

Ø = 6.00 mm bottom
(B)

Ø = 10.00 mm
Ø = 9.00 mm
Ø = 7.50 mm top
(A)

5.50 mm

398

396 side
(C)

Helix pitch = 1.00 mm
Pipe diameter = 0.625 mm
Screw of 5 turns

376

394

398

376

396

390

392

900

10.00 mm 10.00 mm 6.00 mm 6.00 mm

R = 1.00 mm

| Pronasale (0) | Chelion (6, 6) |
|---|---|
| Sellion (1) | Infraorbitale (7, 7) |
| Chin (2) | Zygomatics (8, 8) |
| Menton (3) | Tragions (9, 9) |
| Nasal Roots (4, 4) | Gonions (10, 10) |
| Alares (5, 5) | |

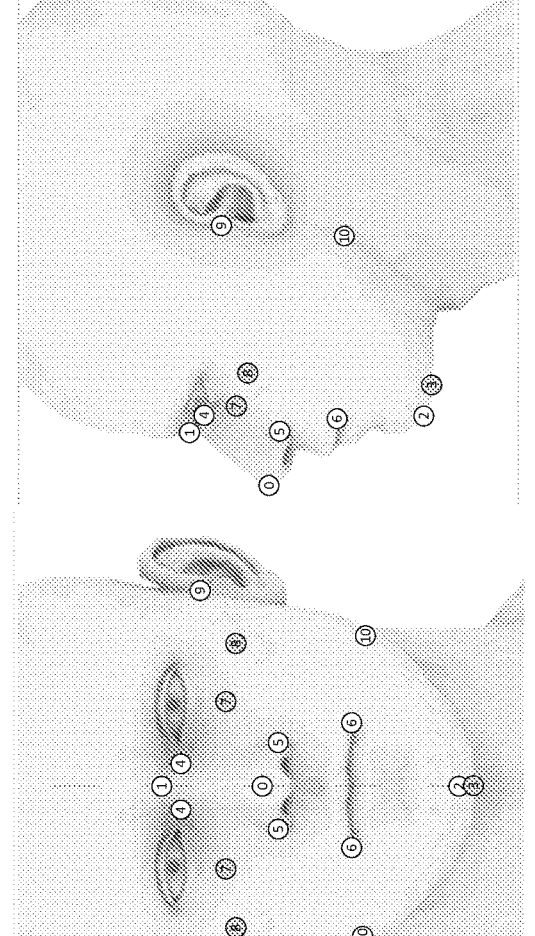

| Nasal root breadth (A) | Bitragion breadth (B) |
|---|---|
| Infraorbitale breadth (C) | Bizygomatic breadth (D) |
| Nose breath (E) | Bigonial breadth (F) |
| Lip breadth (G) | Chin breath (H) |
| Nose length (I) | Sellion-chin length (J) |
| Sellion-menton length (K) | Pronasale-sellion vertical distance (L) |
| Pronasale-subnasale vertical distance (M) | Pronasale-chin vertical distance (N) |
| Pronasale-menton vertical distance (O) | |
| (Six From NIOSH's 21 Dimensions) | |

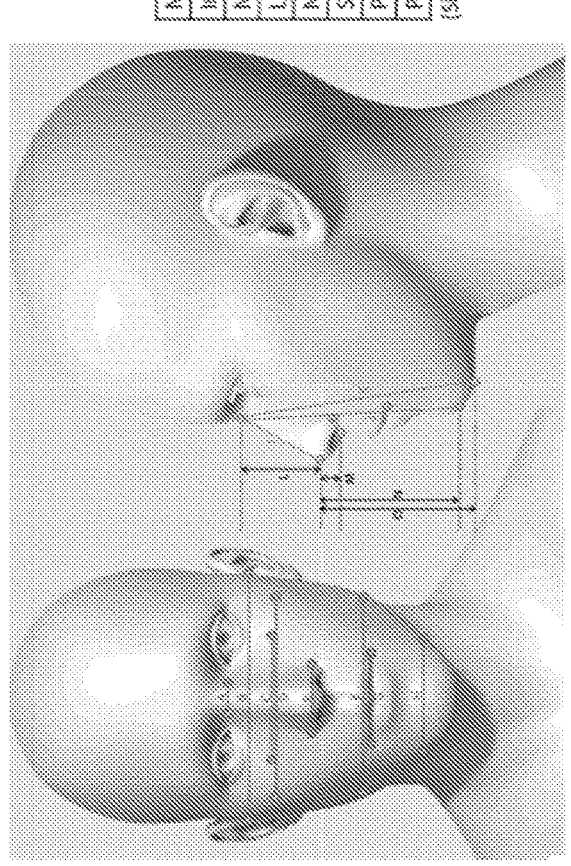

*FIG. 5C*

FROM

--------- COMPUTATION --------→ DERIVED LANDMARKS

THE COMPUTATED POINTS THAT
ARE IDENTIFIED BASED ON
CERTAIN GEOMETRICAL
RELATIONSHIPS ON THE
PROJECTED 2D MAPPINGS.

*INCLUDE*

TOP EDGE POINT (1)
*JAW SIDE POINTS (D2)
*FACE SIDE POINTS (D3)
*JAW POINT (D4)

*INDICATES THE PAIRED
LANDMARKS SYMMETRICALLY
LOCATED ON BOTH FACE SIDES.*

FROM

BASE FRAME
CONTOUR (CONT. 2)*

Side View

Front View

Subject C

Subject B

Subject A

CUSTOM-FIT REUSABLE RESPIRATORY PROTECTIVE DEVICE

RELATED APPLICATION

This application claims priority to, and the benefit of, U.S. Provisional Patent Application No. 63/304,893, filed Jan. 31, 2022, entitled "RESPIRATOR WITH CONTINUOUS FIT MONITORING," which is hereby incorporated by reference herein in its entirety.

STATEMENT REGARDING FEDERALLY SPONSORED RESEARCH OR DEVELOPMENT

This invention was made with government support under Contract Number: 75D30120C09567 awarded by the Centers for Disease Control and Prevention. The government has certain rights in the invention.

BACKGROUND

Workers and healthcare professionals are required to wear respiratory protective devices (RPD) in various workplaces and medical settings throughout the United States. A respiratory protective device (RPD) protects workers against insufficient oxygen environment, and harmful inhalation hazards, such as dust, fog, smoke, mist, gas, vapor, spray, and biological hazards or weapons.

Respiratory protective devices protect the user in two basic ways. The first class of devices protects the user by removing contaminants from the air. This first class of devices includes particulate respirators, which filter out airborne particles, and air-purifying respirators with cartridges/canisters, which filter out chemicals, biological material, and gases. The second class of devices protects the user by supplying clean respirable air from another source. This second class of devices includes airline respirators, which use compressed air from a remote source, and self-contained breathing apparatus (SCBA), which include their own air supply.

One type of respiratory protective device includes filtering facepiece respirators (FFRs) which can be configured with different types of filter configurations, N95, N99, N100, R95, R99, R100, P95, P99, P100, and HE. Filtering facepiece respirators (FFRs) are manufactured in discrete sizes, which are limited in accommodating the size, gender, and ethnic diversity of the user population. The pressure exerted by a respiratory protective device, such as an N95 full-face respirator, on the face seal influences the comfort and tolerability of the user. The pressure can also change during use, potentially compromising the fit of the FFR.

There is a benefit and/or a need to improve respiratory protective devices and their usage.

SUMMARY

An exemplary apparatus and method are disclosed for a respiratory protective device customized to the facial profile of a user to ensure proper fit and operation of the device. The exemplary apparatus and method employ a facial model that uses anthropometric taxonomy aspects of the person's face and measurements from facial scans or fit. The facial model has been modeled to ensure seal even during natural facial movements, e.g., talking, smiling, yawning, etc. The customization can employ rapid three-dimensional fabrication technology that can generate RPDs for adults as well as for children, for whom no FFRs are currently commercially available.

In some embodiments, the exemplary respiratory protective device is configured to be reusable, e.g., designed to be cleaned/sanitized and to use replaceable filtering elements.

In an aspect, a respiratory protective apparatus is disclosed comprising a frame having a contour that maintains a breathable filter covering over a facial region of a user, wherein the frame or contour extends over both upper-cheek regions of a person, over both mid-cheek regions of the person, and a chin region of the person, wherein the frame is customized to a scanned facial profile of the person.

In some implementations, the frame has been modeled to maintain the fit or contact with the facial region of the user in a pre-defined set of usage, including (i) a natural state of the facial region and (ii) and at least one of a talking state, a smiling state, and yawning state of the facial region.

In some implementations, at least a portion of the contour is over, or in proximity to, at least one of: a pronasale facial region, a sellion facial region, or a region therebetween; an infraorbitale facial region, a zygomatic facial region, or a region therebetween; a chin point facial region, a gonion facial region, or a region therebetween; or a menton facial region, a sagittal plane, or a region therebetween.

In some implementations, the breathable filter is coupled to the frame and has a desired pre-defined filtration configuration.

In some implementations, the breathable filter is replaceable.

In some implementations, the pre-defined filtration configuration includes a particulate filtration efficiency of 95% or greater.

In some implementations, the frame comprises a sensor network configured to assess or monitor fit.

In some implementations, the apparatus further includes a set of screws, including a first screw and a second screw, wherein the first screw is configured to be attached to a screw recess located in the frame to maintain the breathable filter covering in the contour of the frame.

In some implementations, the apparatus further includes integral fastening hooks and attachable adjustable straps, the straps comprising a marking scale for customizing and controlling the pressure exerted by the frame on the facial region of the user, and a fastening hub coupled to the fastening hooks and the attachable straps.

In some implementations, the frame is constructed via additive manufacturing using elastomeric materials.

In another aspect, a respiratory protective apparatus is disclosed, the apparatus comprising a frame having a contour that maintains a breathable filter covering over a facial region of a user, wherein the frame or contour extends over both upper-cheek regions of a person, over both mid-cheek regions of the person, and a chin region of the person, including over at least or over an infraorbitale, a zygomatic, a face side point, an upper jaw side point, and a lower jaw point to maintain fit continuously with a person's face throughout use and facial movements.

In another aspect, a method of fabricating a respiratory protective device is disclosed, the method comprising: acquiring (i) a set of images or scans of a user or (ii) a scanned facial profile of the user; generating, by a processor, a model of the facial profile of a facial region of the user based on (i) the set of images or scans of the user or (ii) the scanned facial profile of the user; determining, by the processor, a plurality of anatomical facial landmarks, and landmarks derived therefrom, wherein the plurality of anatomical facial landmarks, and landmarks derived therefrom, include an upper-cheek region of the user, a mid-cheek region of the user, and a chin region of the user; determining, by the processor, using the determined plurality of anatomical facial landmarks, and landmarks derived therefrom, at least one of a frame or a contour thereof that can be fit-ably placed on the user that extends over both upper-cheek regions of a person, over both mid-cheek position regions of the person, and a chin region of the person, wherein the at least one of the frame or the contour thereof is employed in one or more manufacturing operations to manufacture or fabricate the frame having the contour that maintains a breathable filter covering over the facial region of the user.

In some implementations, the plurality of anatomical facial landmarks and landmarks derived therefrom is determined by a first algorithmic process.

In some implementations, the at least one of a frame or the contour thereof is determined by a second algorithmic process.

In some implementations, the one or more manufacturing operations comprise injection molding with elastomeric materials.

In some implementations, the method further includes determining, by the processor, fastening hooks on the frame by a third algorithmic process.

In some implementations, the frame comprises a material compatible with a decontaminating operation comprising ultraviolet (UV) radiation or cleaning solvents.

In some implementations, the frame includes at least a portion of the contour placed at a derived facial landmark on a user's facial anatomy, wherein the contour is over, or in proximity to, at least one of: a pronasale facial region, a sellion facial region, or a region therebetween; an infraorbitale facial region, a zygomatic facial region, or a region therebetween; a chin point facial region, a gonion facial region, or a region therebetween; or a menton facial region, a sagittal plane, or a region therebetween.

In another aspect, a method is disclosed, the method comprising: acquiring (i) a set of images or scans of a user or (ii) a scanned facial profile of the user; generating, by a processor, a model of the facial profile of a facial region of the user based on (i) the set of images or scans of a user or (ii) the scanned facial profile of the user; determining, by the processor, a plurality of anatomical facial landmarks, wherein the plurality of anatomical facial landmarks include an upper-cheek region of the user, a mid-cheek position region of the person, and a chin region of the person.

In some implementations, the method further includes determining, by the processor, a plurality of landmarks derived from the anatomical facial landmarks, wherein the plurality of derived landmarks include: a pronasale facial region, a sellion facial region, or a region therebetween; an infraorbitale facial region, a zygomatic facial region, or a region therebetween; a chin point facial region, a gonion facial region, or a region therebetween; or a menton facial region, a sagittal plane, or a region therebetween.

In another aspect, a method is disclosed, the method comprising: providing a respiratory protective apparatus comprising a frame having a contour that maintains a breathable filter covering over a facial region of a user; measuring a facial region of the user to obtain a plurality of anatomical facial landmarks; and fitting the frame or the contour to the facial region of the user such that the plurality of anatomical facial landmarks is adequately covered or in contact with one of the frames or the breathable filter covering.

BRIEF DESCRIPTION OF DRAWINGS

The skilled person in the art will understand that the drawings described below are for illustration purposes only.

FIGS. 5A-5E illustrate an example method to generate a customized respiratory protective device from a model, according to one or more implementations.

DETAILED DESCRIPTION

Each and every feature described herein, and each and every combination of two or more of such features, is included within the scope of the present disclosure, provided that the features included in such a combination are not mutually inconsistent.

Example System

Figure 1:
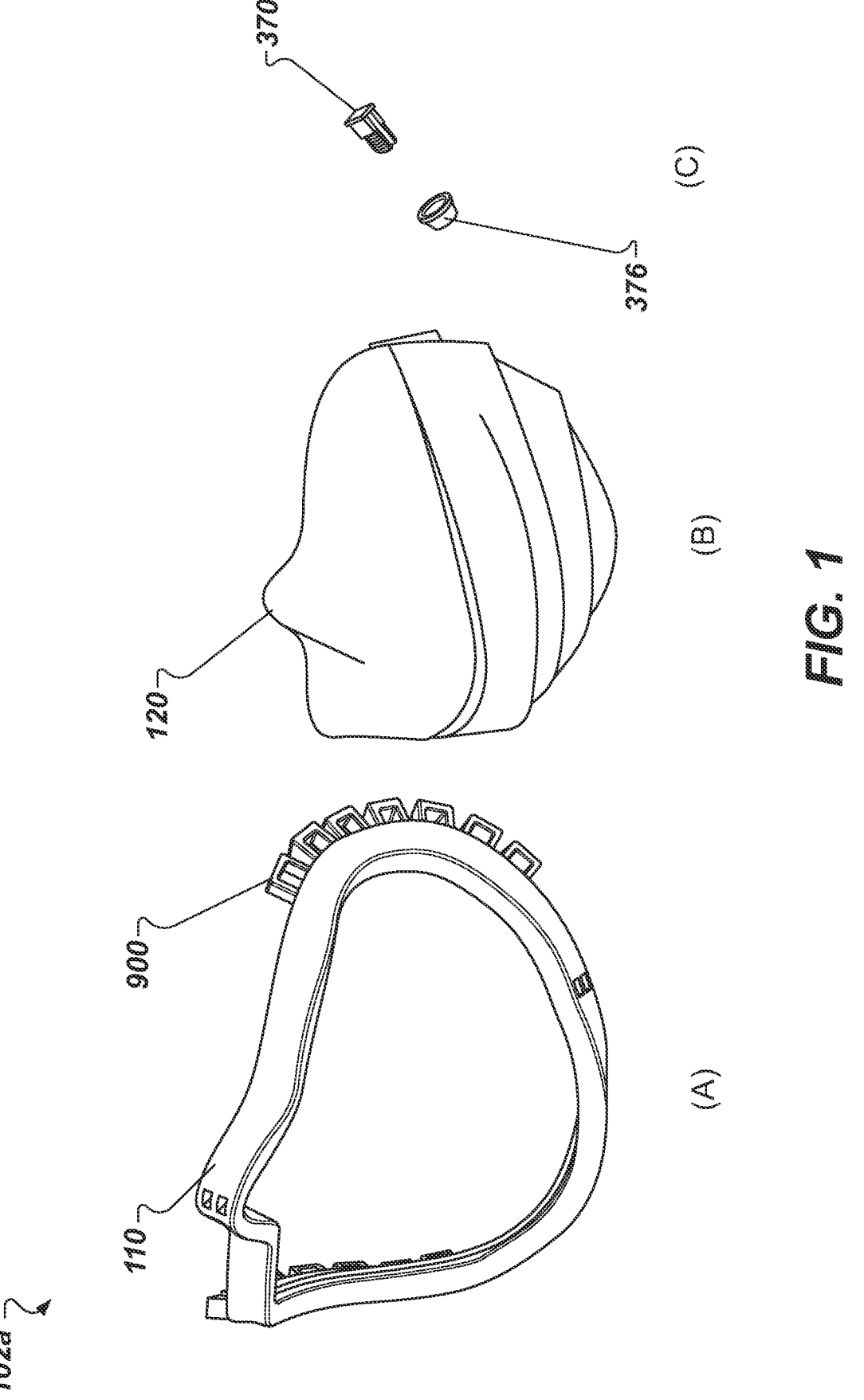
FIG. 1 shows a digital model of the respiratory protective device according to one implementation.

FIGS. 1 and 2 illustrate an example of a respiratory protective device (RPD) 102 (shown as 102a, 102b, respectively) customized to the facial profile of a user to ensure proper fit and operation of the device even during facial movement by the wearer. FIG. 2 shows the RPD of FIG. 1 configured with integrated sensors, e.g., to monitor fit. The respiratory protective device (e.g., 102a, 102b) may be customized for a specific person or to fit a certain person or group of persons (e.g., a hypothetical person or a set of persons of different facial sizes). The frame 110 is shaped to account for the taxonomical features of a person to ensure fit and seal even with facial movements. The frame 110 is configured to be reusable, e.g., designed to be cleaned/sanitized and to use replaceable filtering elements.

In the example shown in FIG. 1, the respiratory protective device 102a includes a frame 110 (e.g., custom fit or otherwise as described herein) to receive a breathable filter 120 configured to filter particulates from the air. In some implementations, the breathable filter 120 is a replaceable filter with a pre-defined filtration configuration having a desired particulate filtration efficiency. In some implementations, the desired particulate filtration efficiency is 95% or greater (e.g., an N95 or P100 mask filtration). Other filter configurations may be used, e.g., N95, N99, N100, R95, R99, R100, P95, P99, P100, HE, among others described herein.

As noted above, the frame 110 is shaped to account for the taxonomical features of a person to ensure fit and seal even with facial movements. In FIG. 1, the frame 110 is shaped to have a contour over at least or over an infraorbitale, a zygomatic, a face side point, an upper jaw side point, and a lower jaw point to maintain fit continuously with a person's face throughout use and facial movements.

As noted above, the frame 110 is configured to be reusable, e.g., designed to be cleaned/sanitized and to use replaceable filtering elements. In FIG. 1, the respiratory protective device 102 also includes a set of screws 370 and screw caps 376 that may be employed to secure the breathable filter 120 to the frame 110.

Sensor-integrated RPD. As noted above, FIG. 2 shows the same RPD configured with integrated sensors, e.g., to monitor fit. The sensor-integrated respiratory protective device 102b includes the frame 110 (now referenced as 110b) configured as two components: a first portion 112 (shown as a "base frame") and a second portion 114 (shown as a "covering piece") that, when joined, collectively forms a contour over a person's face to ensure a fit to the user's facial structure and to retain the breathable filter 120.

The respiratory protective device 102b includes within the frame 110b a number of hollow spaces (shown as cavities 109a-109e to accommodate a sensor network 103. Such a sensor network 103 may aid in monitoring the fit of the respiratory protective device 102b on a user's face.

The respiratory protective device 102b includes a signal processing module to receive signals (e.g., analog pressure signals) from the sensor network 103 to perform the analog-to-digital conversion (ADC) and to generate alerts based on that measurement. The signal processing module may communicate, over a wired or wireless communication channel, to a local controller, monitoring devices, and/or cloud infrastructure that can provide access to the measurement data and/or alerts. Additional examples of the sensor-integrated respiratory protective device and its operations may be found in U.S. Patent Application, entitled "RESPIRATORY PROTECTIVE DEVICE WITH CONTINUOUS FIT MONITORING," concurrently filed herewith, having application Ser. No. 18/162,312, which is hereby incorporated by reference herein in its entirety.

Figure 2A:
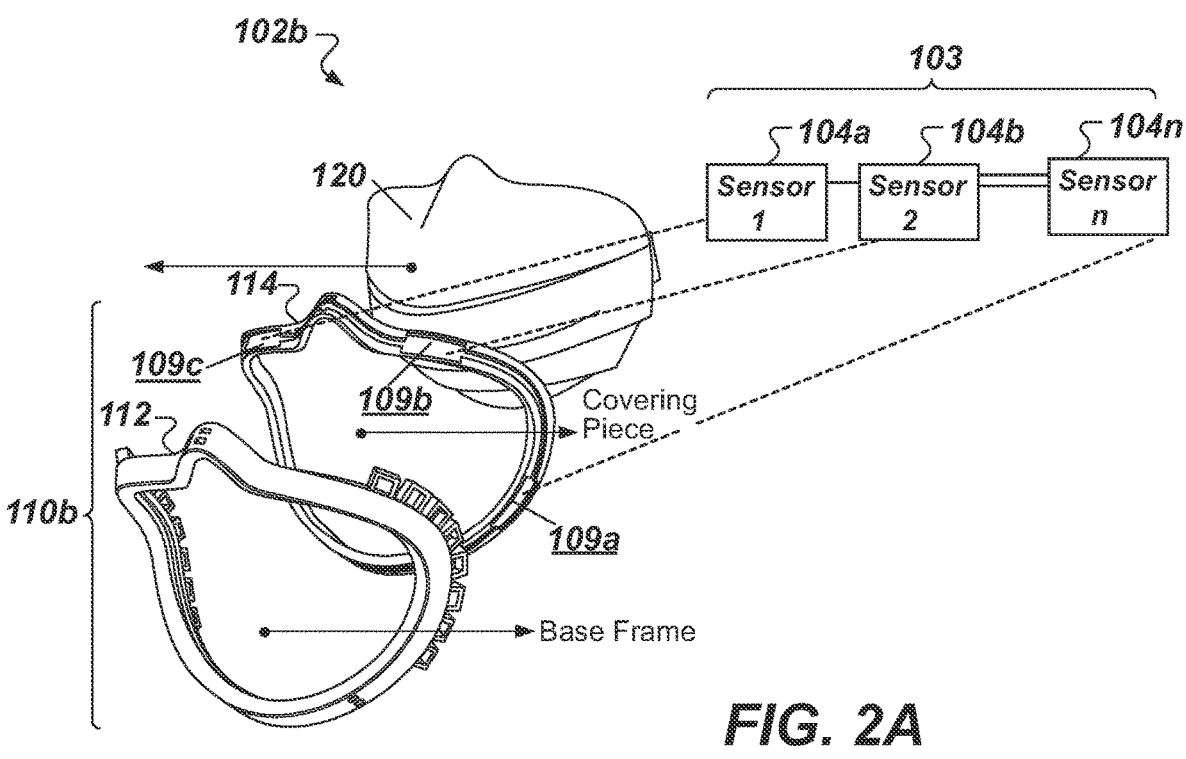
FIGS. 2A-2B illustrate an example of a continuous fit monitoring system for a sensor-integrated respiratory protective device (RPD) or customizable device of the same, in accordance with an illustrative embodiment.
Figure 2B:
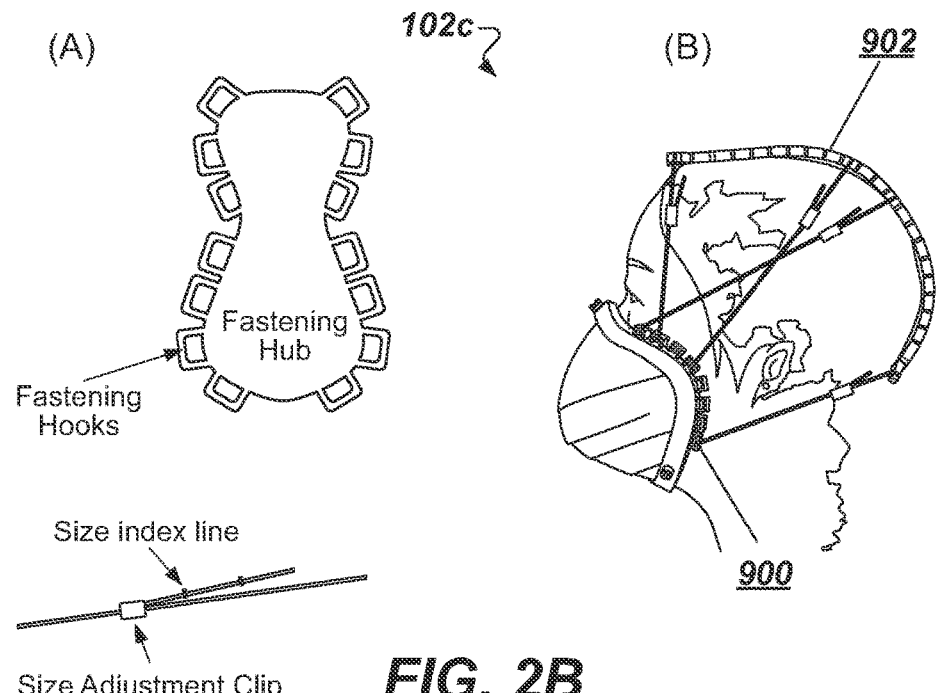

Improved Fit with Fastening Hub. In the example shown in FIG. 2A, the frame 110 is shown included with additional optional features that may be employed to improve the fit and operation of the device. In FIGS. 2A and 2B, the frame 100 further includes an array comprising two or more fastening hooks 900 that can be used to couple with straps to wrap around a person's head, e.g., in conjunction with a fastening hub 902 placed at the back of the person's head. The fastening hub and straps are shown in FIG. 2B, subpanel (A), while FIG. 2B, subpanel (B), shows an example of the RPD (e.g., 102a, 102b) operating with a fastening hub. Additional description of the hub and hooks may be found in U.S. Patent Application, entitled "FASTENING HUB FOR ENHANCING THE FIT AND COMFORT OF A RESPIRATORY PROTECTIVE DEVICE," concurrently filed herewith, having application Ser. No. 18/162,323, which is hereby incorporated by reference herein in its entirety.

Example Sensor-Integrated Respiratory Protective Device #1

Figure 3A:
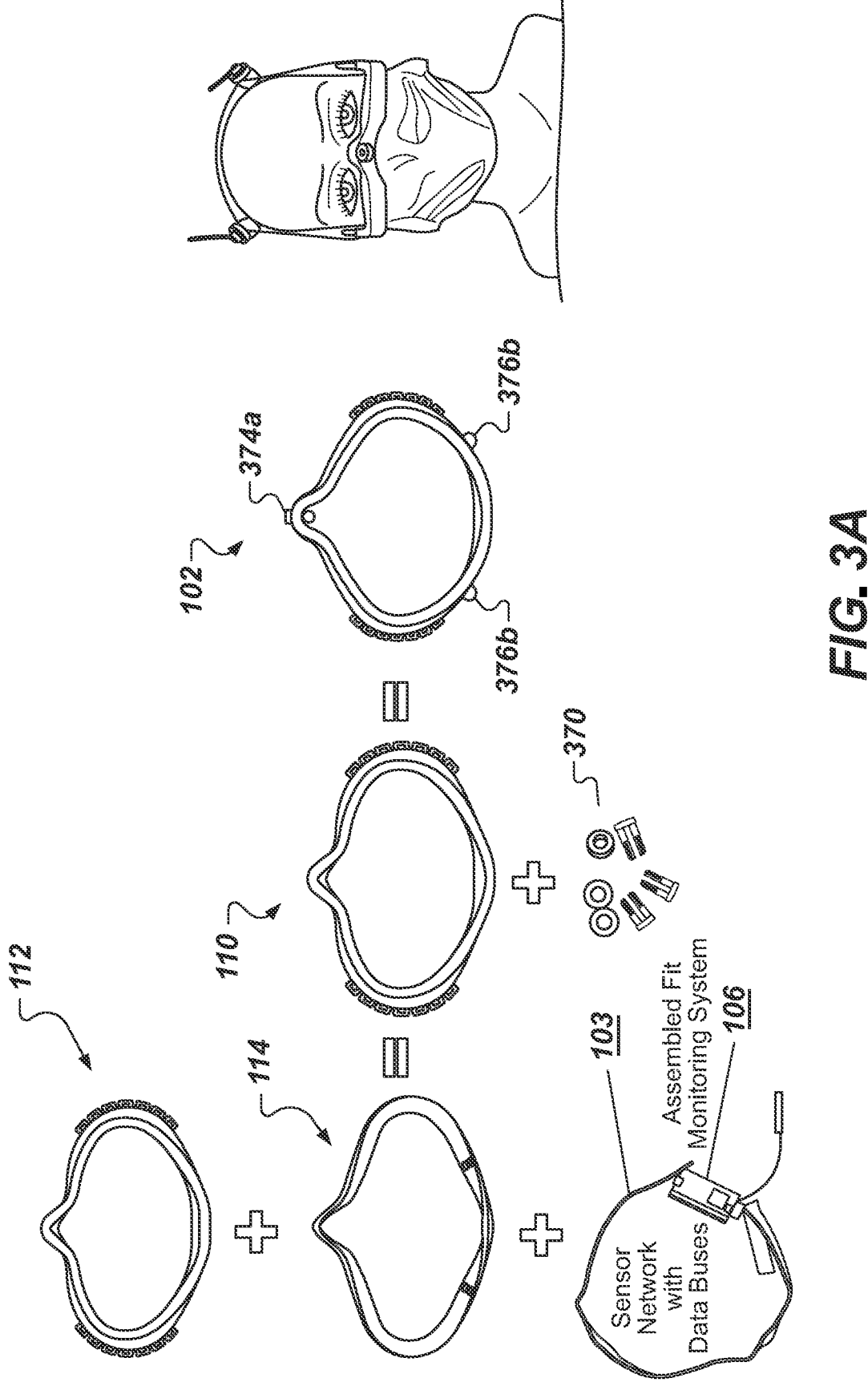
FIGS. 3A-3T are diagrams of example mechanical designs of components of a sensor-integrated respiratory protective device configured for continuous fit monitoring, e.g., of FIG. 1 or 2, according to various implementations.
Figure 3B:
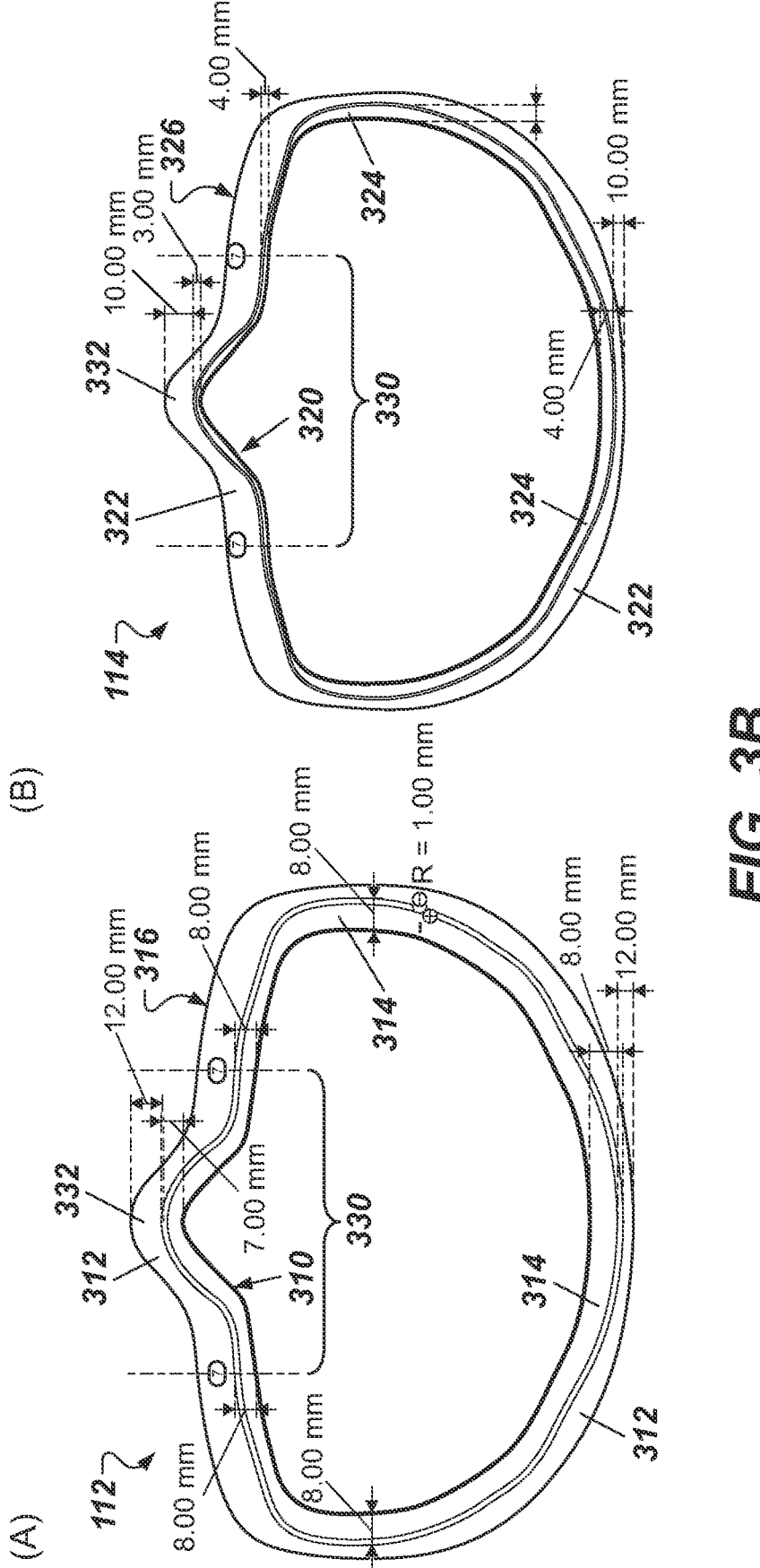
Figures 3C, 3D:
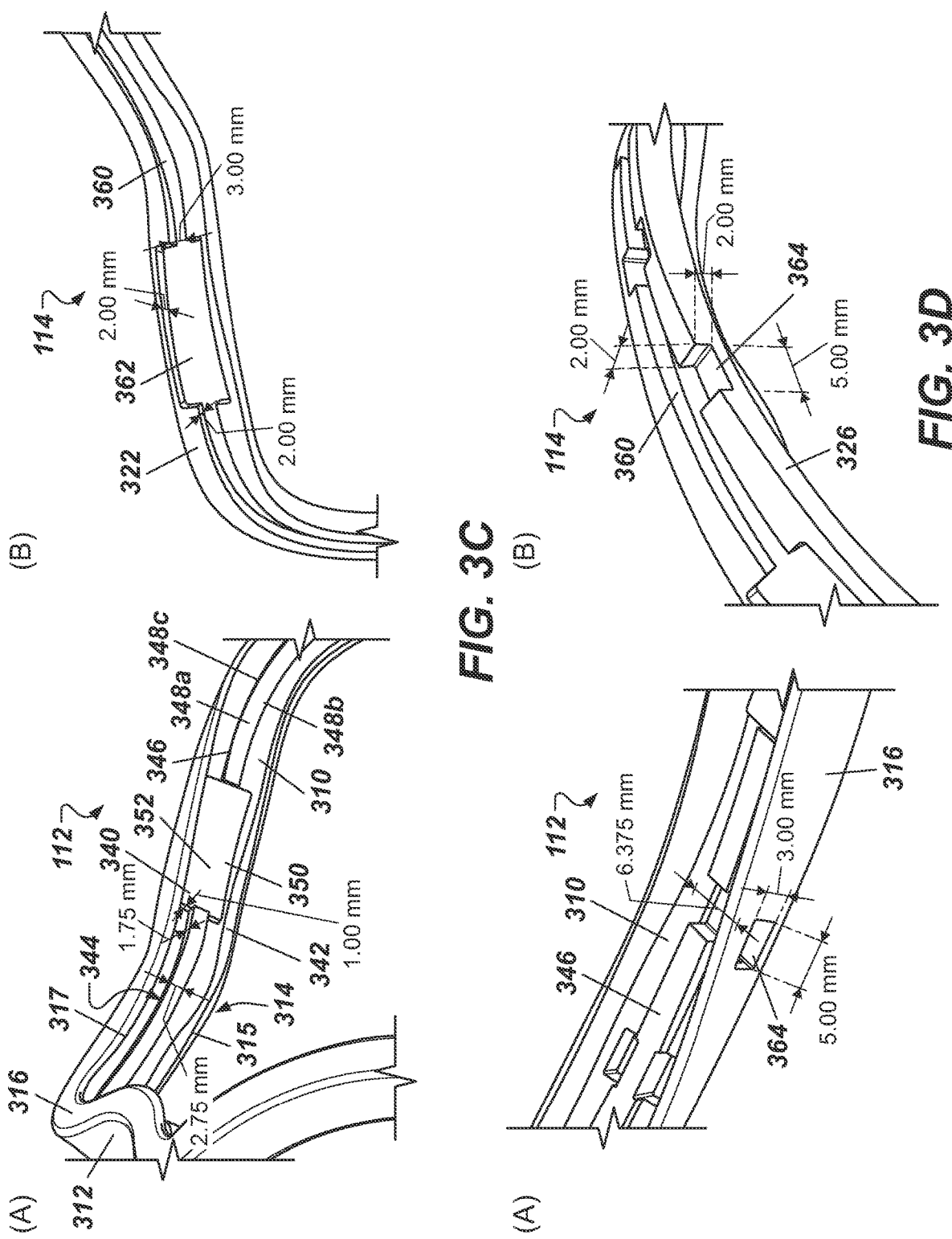
Figure 3E:
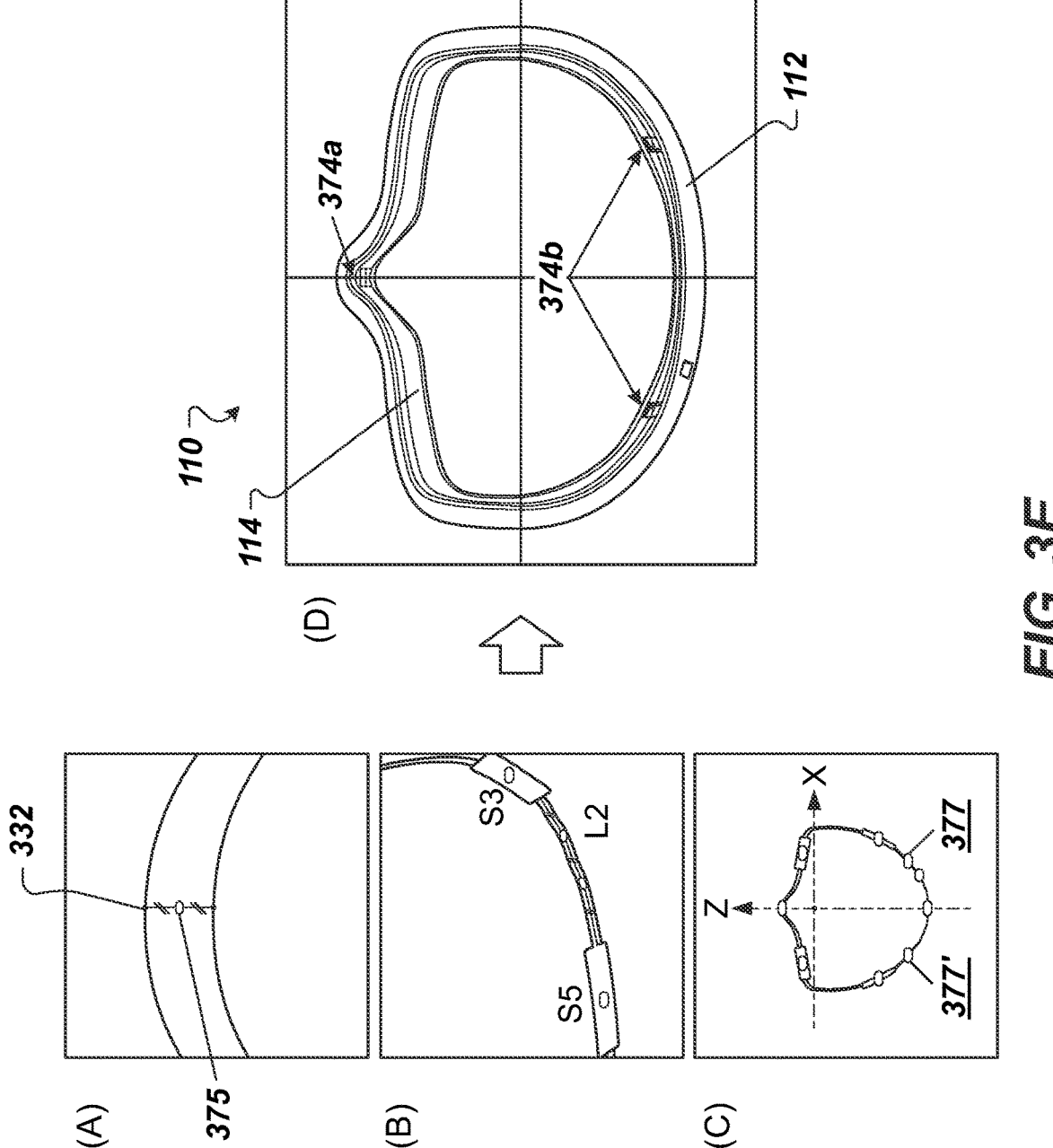
Figure 3F:
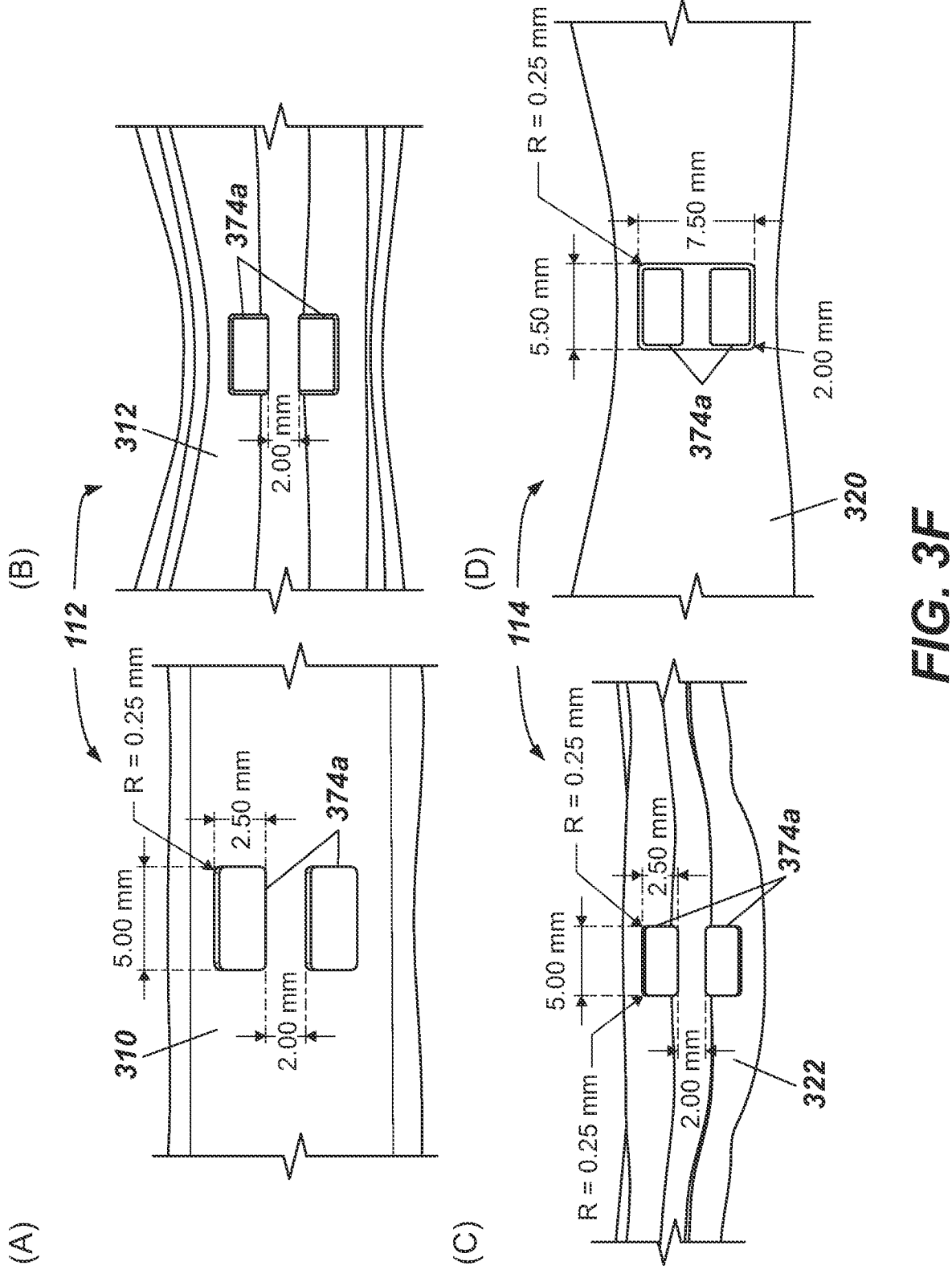
Figure 3G:
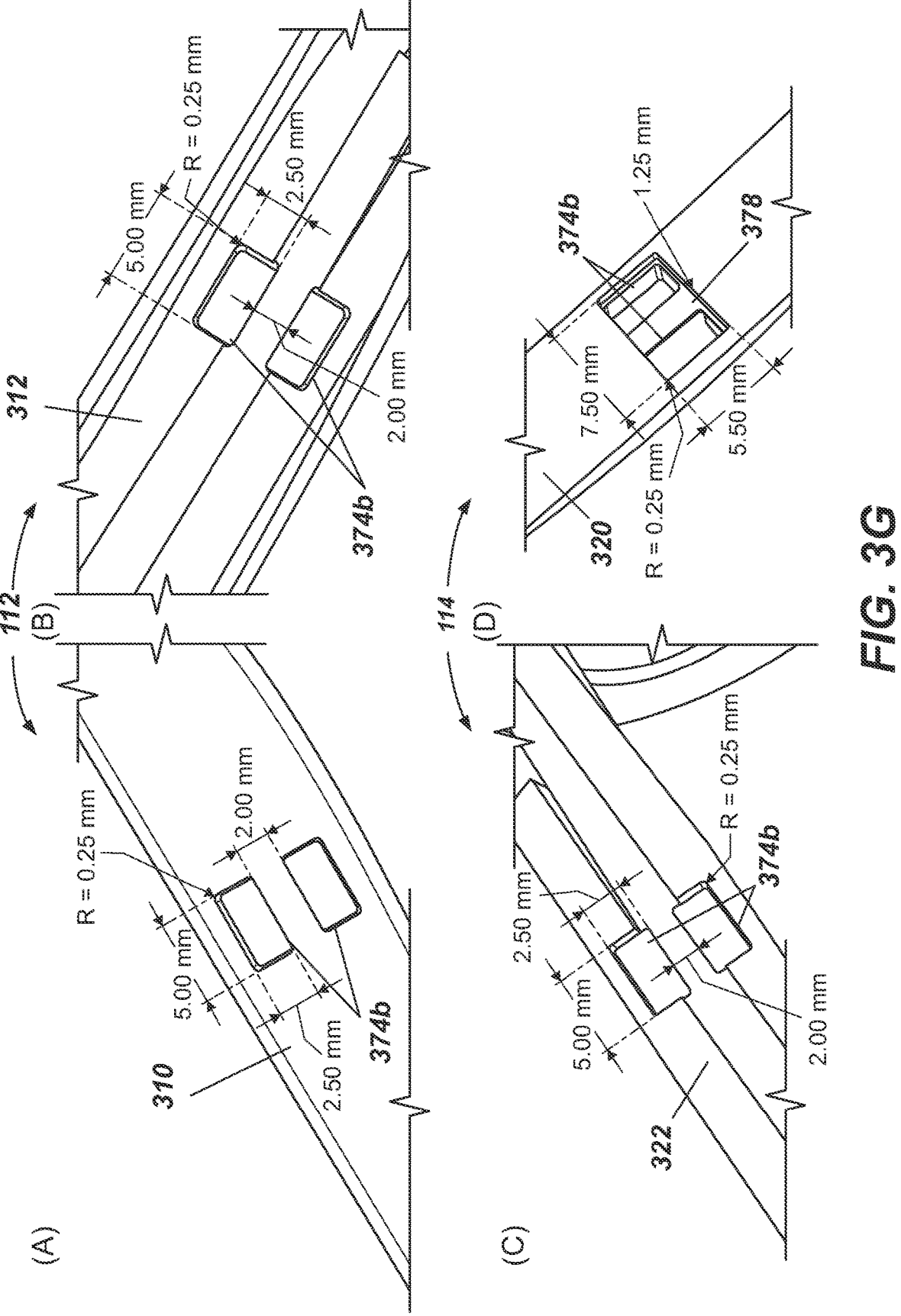
Figures 3H, 3I:
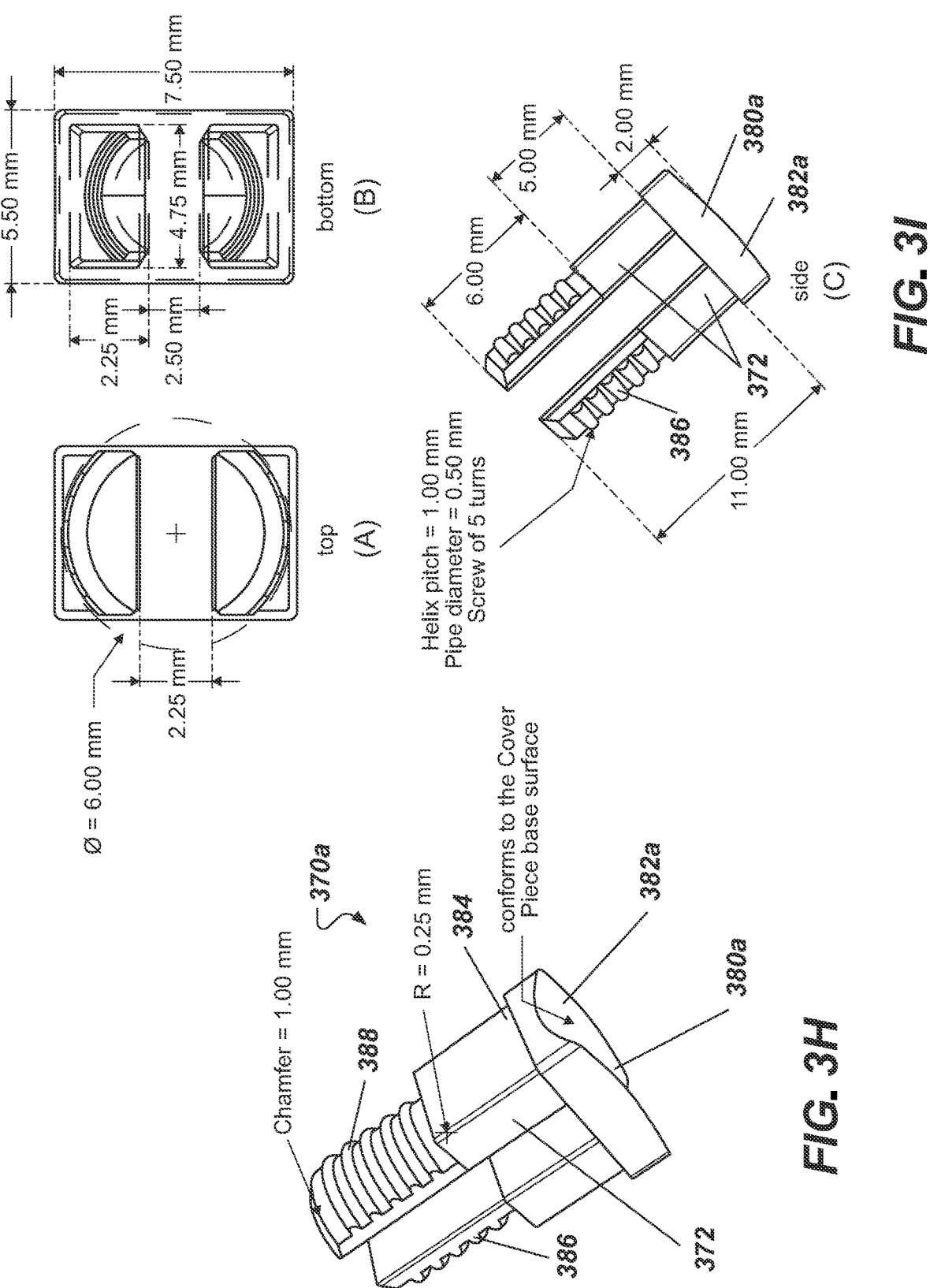
Figures 3L, 3M:
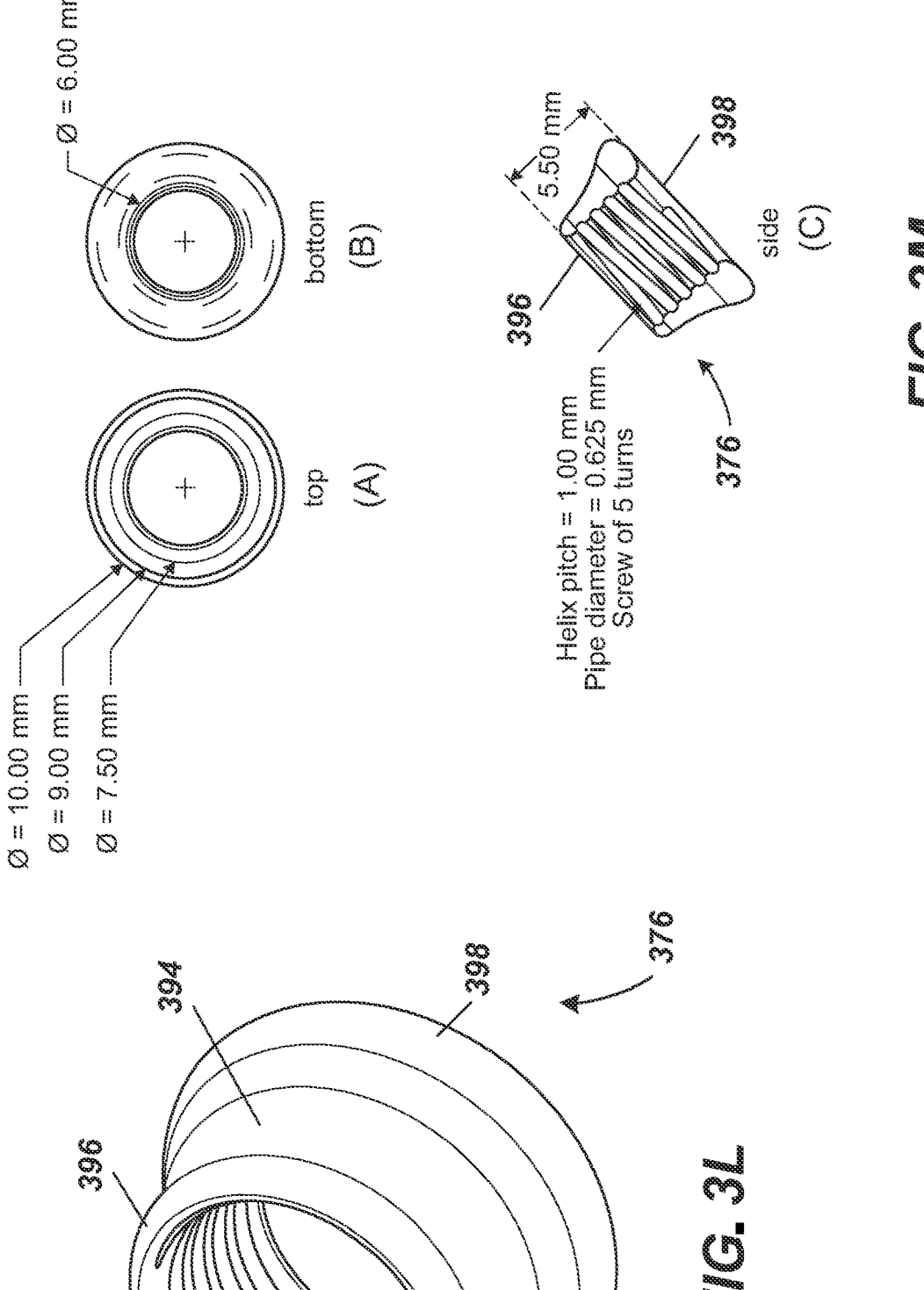
Figure 3O:
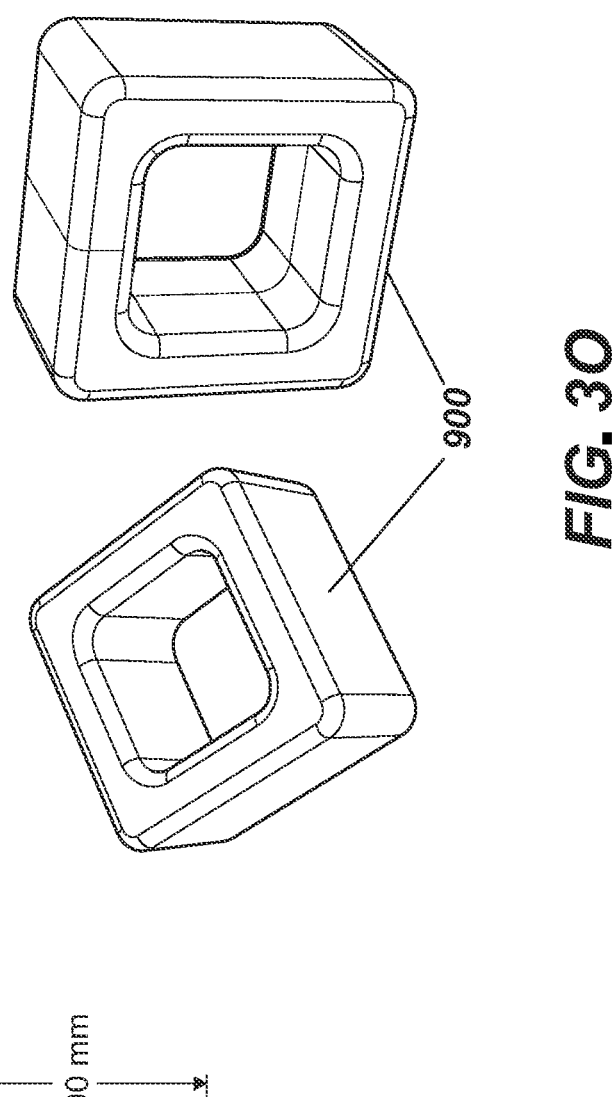
Figure 3N:
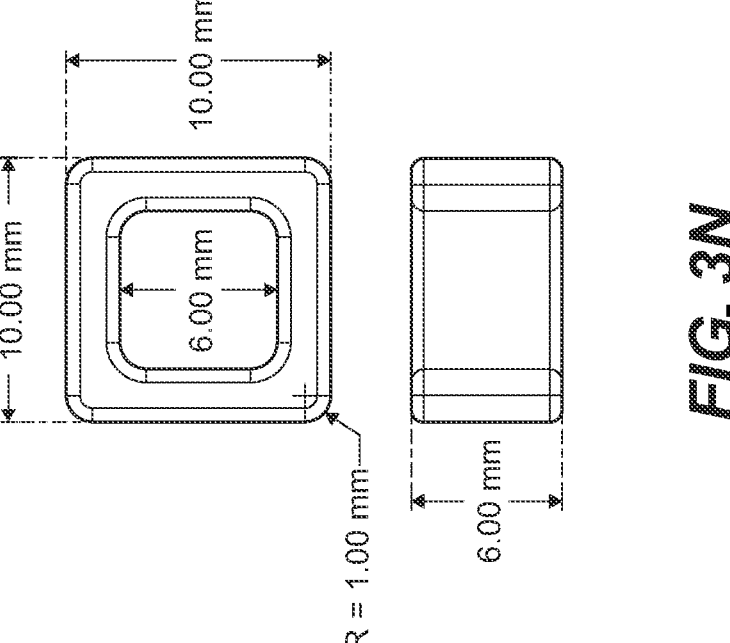
Figures 3P, 3Q:
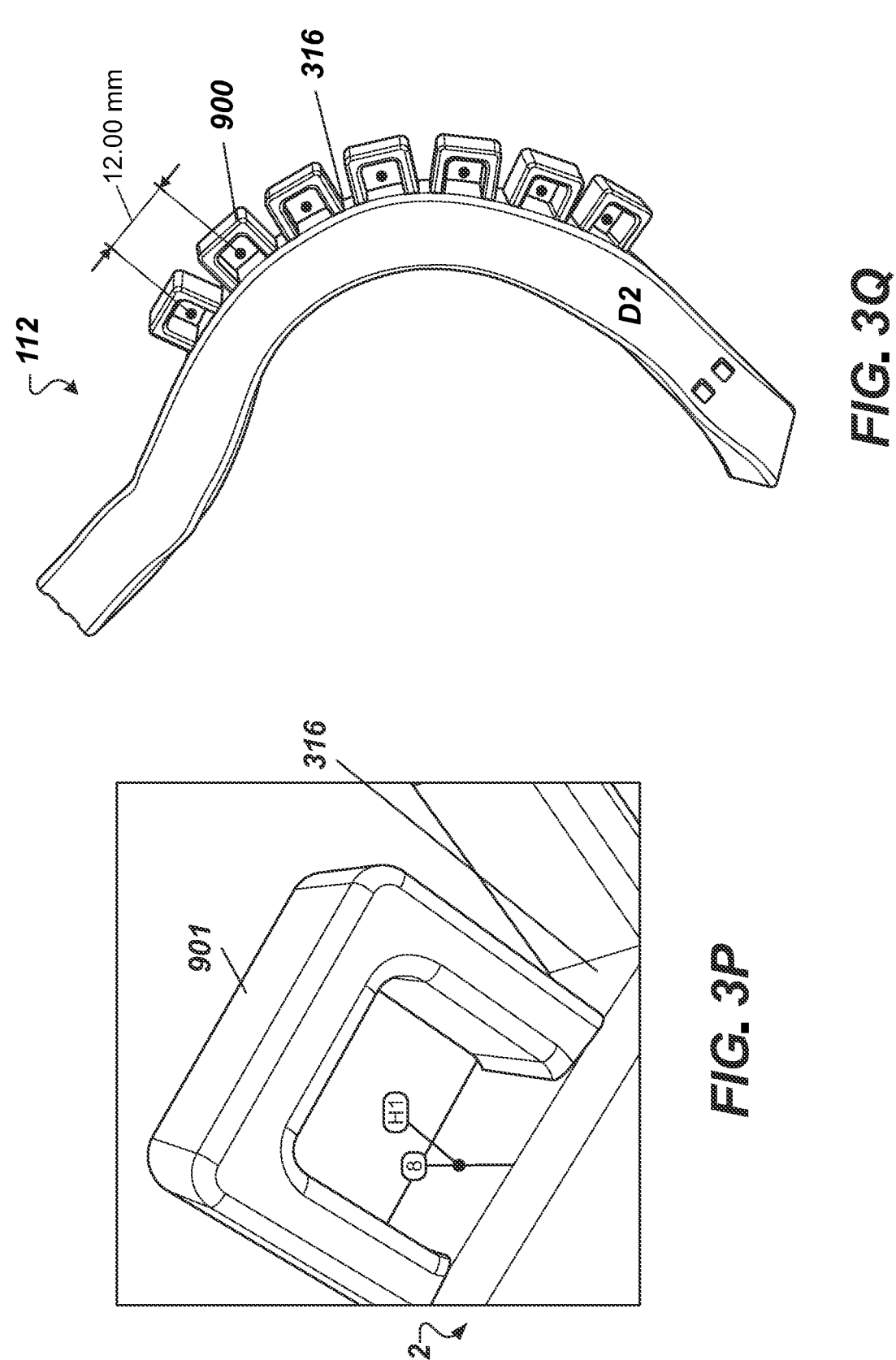
Figures 3R, 3S:
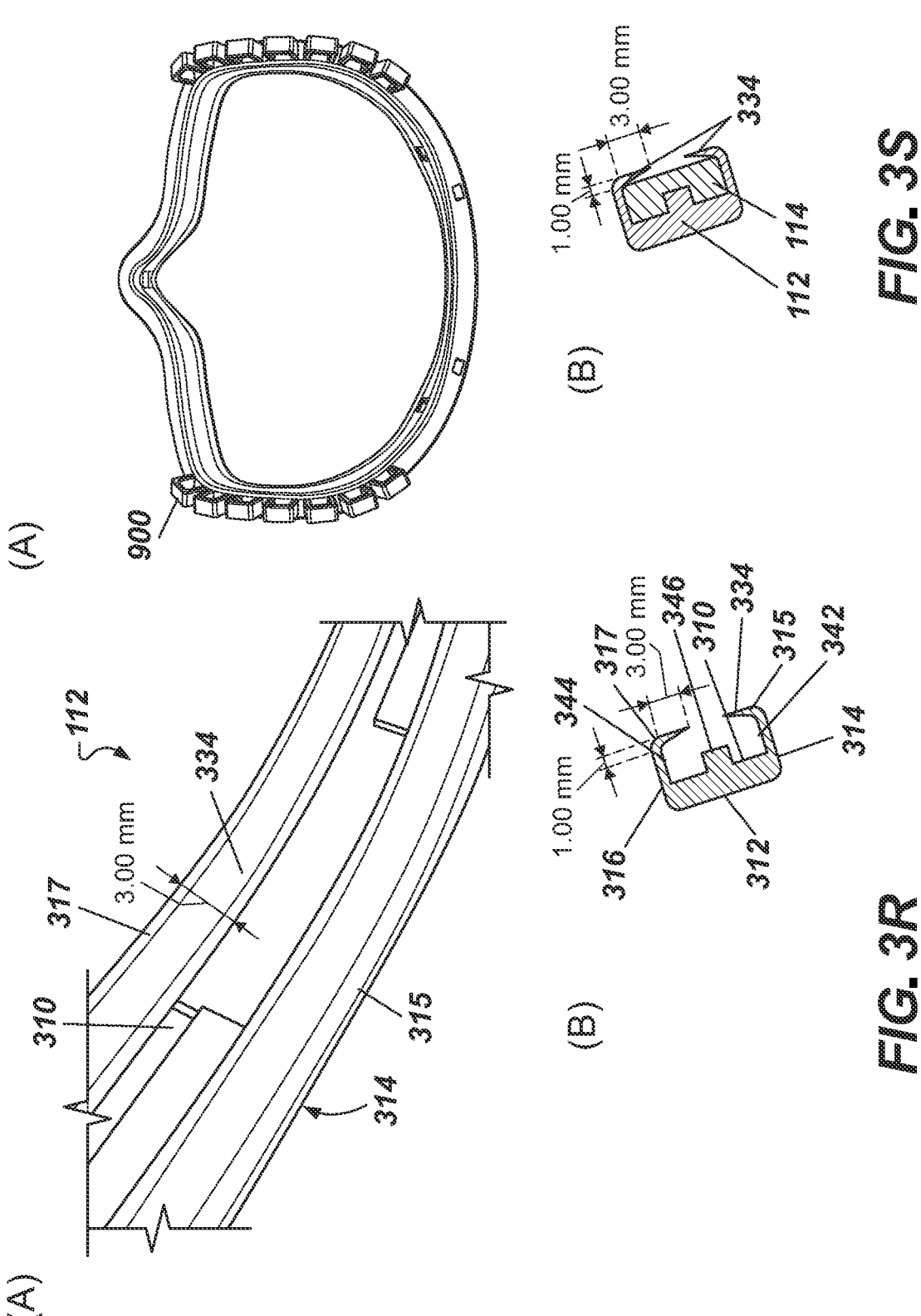
Figure 3T:
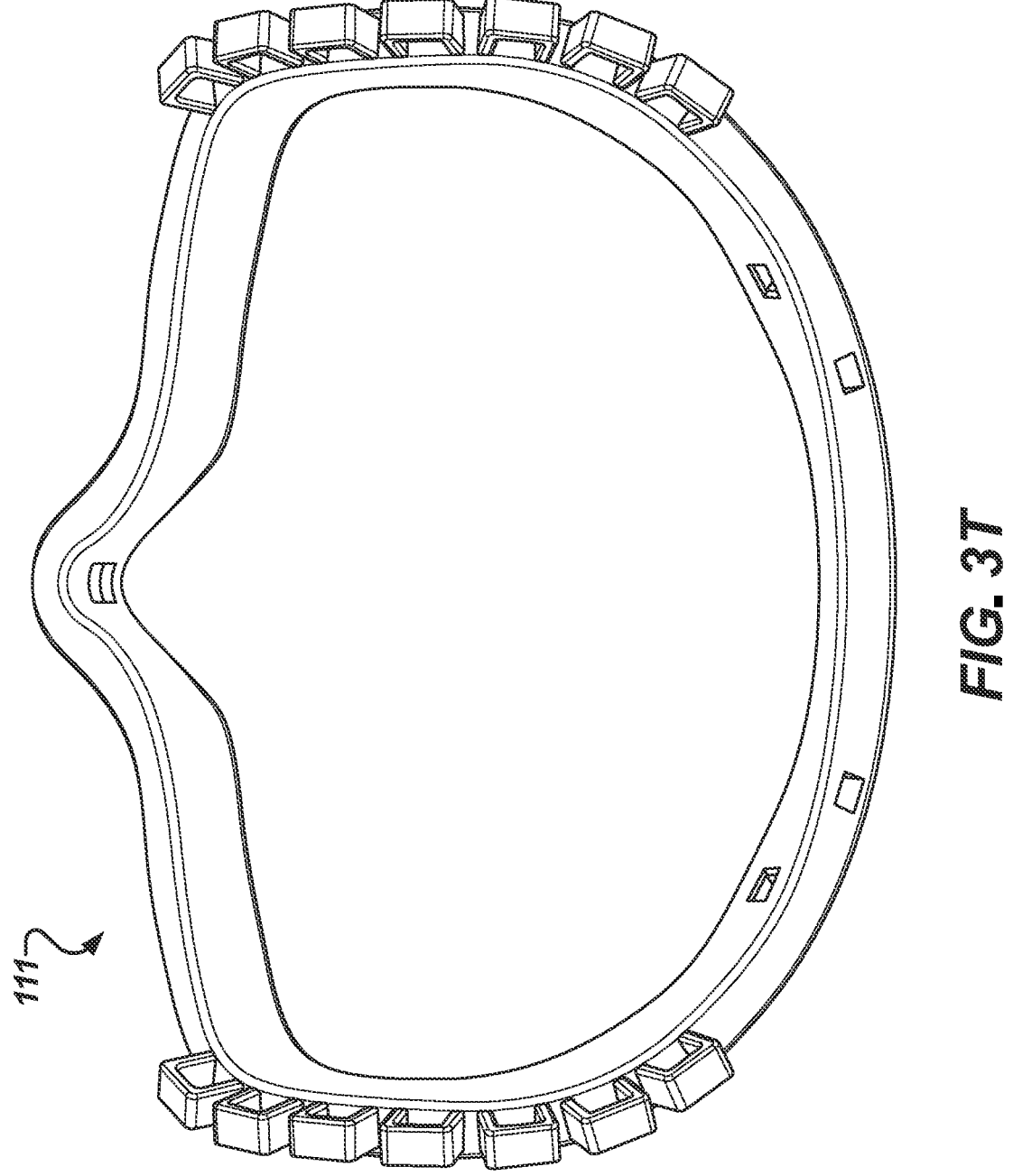

FIGS. 3A-3T are diagrams of example of mechanical designs of various components and examples of processes to design the same of a sensor-integrated respiratory protective device configured for continuous fit monitoring, e.g., of FIG. 1 or 2, according to various implementations. FIG. 3A shows an implementation of the components and their integrations to form the sensor-integrated respiratory protective device. FIGS. 3B, 3C, and 3D show details of the frame. FIGS.

3E-3G show details on the screw holes. FIGS. 3H-3M show details on the screws and screw cap. FIGS. 3N-3Q show details on the fastening hook that may be integrated into the device. FIGS. 3R and 3S show details on frame construction and design. FIG. 3T shows a second embodiment of the sensor-integrated respiratory protective device as a single unitary structure.

System Design. FIG. 3A shows an implementation of the components and their integrations to form the sensor-integrated respiratory protective device. Like numbering between FIGS. 3A-3T (as well as other figures) represent like-elements to those shown in other figures within this document. In the example shown in FIG. 3A, the frame 110 comprises two components: a base frame 112 and a covering piece 114 that can be separately manufactured and embedded with the sensors and electronics (shown collectively as 103) prior to final assembly. The construction includes a set of re-attachable screw sets 370 that can facilitate the quick removal and attachment of the breathable filter while maintaining the seal for the highest level of respiratory protection level when desired. The frame 110 may be readily manufactured to provide customized face wear and protection for the user or may be manufactured for different facial shapes and sizes to be fitted for the person.

Frame. FIGS. 3B, 3C, and 3D show details of the frame 110 formed of the base frame 112 and covering piece 114. In FIG. 3B, the base frame 112 shown in subpanel (A) includes a base inner surface 310, as the back of the component, that would mate with the covering piece 114, shown in subpanel (B). The base outer surface 312, as the front of the component, forms the outer surface of the frame 110 and of the device 102 in the final assembled form. The base inner surface 310 and base outer surface 312 are substantially parallel to the face surface.

The base frame 112 includes a first base surface 314 that forms an interior side of the base frame, located between the base inner surface 310 and the base outer surface 312 (e.g., closer to a filtering component to be placed at the center of the base frame 112). The base frame 112 includes a second base surface 316 (see FIG. 3D) located opposite and spaced apart from the first base surface 314, extending between the base outer surface 312 and the base inner surface 310 on an exterior side of the base frame 112 (e.g., further away from the center of the base frame 112). In other words, the first base surface 314 and the second base surface 316 can be viewed as extending out from a user's face and are substantially perpendicular to the face surface.

The covering piece 114 includes a structure having a corresponding shape to that of the base frame 112 and includes (i) a cover inner surface 320 to be placed in contact with the user's face and (ii) a cover outer surface 322 to mate with the base frame 112 and the base inner surface 310. Both the cover inner surface 320 and the cover outer surface 322 can be characterized as being substantially parallel to the face surface. The covering piece 114 includes (iii) a first cover surface 324 that connects between the cover inner surface 320 and the cover outer surface 322 on an interior side of the covering piece 114 (e.g., closer to a filtering component in the center of the base frame 112) and (iv) a second cover surface 326 located opposite and spaced apart from the first cover surface 324, extending between the cover outer surface 322 and the cover inner surface 320 on an exterior side of the covering piece 114 (e.g., further away from the center of the base frame 112). The first cover surface 324 and the second cover surface 326 can be characterized as extending out from a user's face by being substantially perpendicular to the face surface.

The base frame 112 and covering piece 114 each include a nose bridge area 330 that is intended to seat and extend from (i) the infraorbitale (marked as point "7" in FIG. 3B) of the user's face to (ii) the center nose bridge apex 332 of the nose bridge area 330. The nose bridge area 330 includes contours forming an angle converging at a nose bridge apex 332 at the center of the nose bridge area 330.

The depth of the base frame 112, in this design, as measured across the first base surface 314 is 8 mm (essentially defining the depth the base frame 112 would extend from a user's face). At the nose bridge area 330, the depth of the base frame 112 is reduced to 7 mm to reduce the weight and footprint of the base frame 112. The thickness (e.g., outer surface width) of the base frame 112, as measured across the base outer surface 312 is 12 mm (the distance between the first base surface 314 and the second base surface 316). Each of the surface junctions of the base frame 112 has a fillet radius of 1 mm.

The depth of the covering piece 114, in this design, as measured across the first cover surface 324 is 4 mm (essentially defining the depth the covering piece 114 would "stick out" from a user's face). At the nose bridge area 330, the depth of the covering piece 114 is reduced to 3 mm to reduce the weight and footprint. The thickness of the covering piece 114, as measured across the cover outer surface 322, is 10 mm (the distance between the first cover surface 324 and the second cover surface 326). The smaller thickness of 10 mm for the covering piece 114 allows the covering piece 114 to fit snugly into the base frame 112.

Referring to FIGS. 3C and 3D, base frame 112 and covering piece 114 includes network channels 117a, 117b for integration of the sensor network 103. The base frame 12 includes extrusions while the covering piece 114 includes corresponding slots that can (i) facilitate frictional fitting between the two pieces to maintain their attachments during the fabrication of the frame 110 and (ii) accommodate the sensors 104a-104n and their associated data buses or conduit 118. The extrusions and slots may be dimensions to form cavities for the electronics and sensors when the base frame 112 and covering piece 114 are assembled.

In this design, each sensor 104a-104n of the sensor network 103 is disposed close to the covering piece side of the frame 110 and is configured to acquire measurement signals (e.g., pressure, contact, capacitance, or other properties as described herein) to determine such properties at the interface between the user's facial structure and the frame 102. To reduce the number of wires, each sensor 104a-104n is connected to a common power line 122 (shown in FIG. 1A) that is drawn through the conduit 118 to provide power from the signal processing module 106 to each of the sensors 104a-104n. Also, each sensor 104a-104n includes a data line 124 (shown in FIG. 1A) drawn through the conduit 118 for transmitting the measured signals to the signal processing module 106 at the end of a data bus containing each of the sensor data lines 124.

FIG. 3C, subpanel (A), shows a rear view of the base frame 112, and FIG. 3C, subpanel (B), shows the front view of the covering piece 114. It can be observed from the left and right views that a portion of the base frame 112 has extrusions that match with a corresponding portion with cavities or channels of the covering piece 114. It can also be observed that the base inner surface 310 is set back from the edges of the first base surface 314 and second base surface 316 such that a third base surface 342 and fourth base surface 344 extend from the edges 315, 317 of the first and second base surfaces 314, 316 to the base inner surface 310.

The third and fourth base surfaces 342, 344 are substantially parallel to the first and second base surfaces 314, 316, respectively.

It can also be observed that the base inner surface 310 includes a channel extrusion 346 centered on the base inner surface 310 between the third and fourth base surfaces 342, 344. The channel extrusion 346 includes a channel surface 348a separated and spaced apart from the base inner surface 310. In this design, the channel surface 348a is 1.75 mm from the base inner surface 310. The channel extrusion 346 includes a channel side surfaces 348b, 348c opposite and spaced apart from each other and centered about the channel extrusion 346. The channel side surfaces 348b, 348c define the width of the channel extrusion, which in this design is 2.75 mm.

It can also be observed that the base inner surface 310 includes a sensor extrusion 350 centered on the base inner surface 310 between the third and fourth base surfaces 342, 344. The sensor extrusion 350 includes a sensor extrusion surface 352 separated and spaced apart from the base inner surface 310. In this design, the sensor extrusion surface 352 is 1.00 mm from the base inner surface 310.

The cover outer surface 322 of the covering piece 114 includes corresponding slots to accommodate both the extrusions 346, 350 of the base frame 112 and the structure of the sensor network 103. The cover outer surface 322 includes slots or channels 360 to accommodate conduit 118 or wires between sensors 104a-104n. The channels 360 are centered on the cover outer surface 322 between the first and second cover surfaces 324, 326. The channels 360 have a channel depth and a channel width. In this design, the channel depth is 2 mm, and the channel width is 3 mm.

The covering piece 114 also forms a number of sensor cavities 362, on the cover outer surface 322, to accommodate the sensors 104a-104n. The sensor cavity 362 is similarly centered on the cover outer surface 322 and includes a sensor slot depth. In this embodiment, a sensor slot depth is 2.0 mm.

FIG. 3D shows details of a data bus or conduit opening 364 in each of the base frame 112 (in subpanel (A)) and the covering piece 114 (in subpanel (B)). For the sensor network 103 to receive power and transfer data, each sensor 104a-104n is connected to a data line 124 and a common power line 122 (shown in FIG. 1A). At the termination of the sensors 104a-104n, all of the lines 122, 124 form a data bus which then connects to the signal processing module 106. The signal processing module 106 may be connected to an exterior portion of the frame 110. The data bus or conduit 118 may route to the outside of the frame 110, via an exit pathway, to connect with the signal processing module 106.

In FIG. 3D, the conduit opening 364 is formed as a rectangular opening on the second base surface 316 of the base frame 112. In this design, the rectangular opening is 3.0 mm×5.0 mm. The conduit opening 364 extends through a portion of the channel extrusion 346 on the base inner surface 310. The covering piece 114 also includes the conduit opening 364 and also a rectangular cut-out. The rectangular cut-out may extend from the second cover surface 326 to the channel 360. The rectangular cut-out in this design is 2.0 mm×5.0 mm.

While the various components and internal structures of the frame (e.g., channels 360 and cavities 362 for sensors 104a-104n and conduit 118 in the covering piece 114 and the corresponding extrusions 340 in the base frame 112) have been designed to hold each piece of the frame 110 securely, the flexible nature of the materials used for the base frame 112 and covering piece 114 could cause them to separate during use. To minimize or avoid this separation, the frame 110 employs specially designed screw sets 370 as an "interlocking mechanism" to hold the base frame 112 and covering piece 114 together. The screw set 370 includes screw pegs 372 having a length that can pass through the screw holes 374 formed in the base frame 112 and the covering piece 114 to be capped by screw caps 376. The interlocking mechanism can additionally provide a means to secure the breathable filter 120 to the respiratory protective device frame 110 during its use. The screw holes 374 can extend from the base inner surface 310 to the base outer surface 312 and from the cover inner surface 320 to the cover outer surface 322, respectively.

Screw Set Location. In this design, the frame 110 includes three locations for the set screws 370: (i) at the top center (374a), (ii, iii) on either side of the frame 110 (376b). FIG. 3E shows example locations of the three interlocking positions and the locations of the screw holes 374, as shown in subpanel (D). In FIG. 3E, the top center screw hole 374a is formed by first determining a line between two base contours at the top center, coincident with the nose bridge apex 332, as shown in subpanel (A). Then, the midpoint "L1" 375 of that line would be the center point of the top center screw hole 374a. The side screw holes 374b are formed by dividing a first sensor location "S3" and a second sensor location "S5" into three segments: the one-third point from "S3" is marked "L2" 377 as the center point of the side screw hole 374b, as shown in subpanel (B). The other screw hole 374b can be determined at a mirrored position "L3" 377', as shown in subpanel (C).

FIG. 3F (top screw hole) shows example dimensions and configurations of the base outer surface 312 (in subpanel (B)), and base inner surface 310 (in subpanel (A)) for the region associated with top screw holes region 374a. In the base frame 112, the top center screw hole 374a, in this design, is defined by two holes that are 5 mm×2.5 mm with a corner fillet radius of 0.25 mm with a gap distance of 2 mm. In the covering piece 114 (shown in subpanels (C) and (D)), the top center screw hole 374a is also defined by two holes having the same dimensions as that of the base frame 112.

FIG. 3G (side screw hole) shows example dimensions and configurations of the base outer surface 312 for the region associated with the side screw holes 374b. In the base frame 112 (shown in subpanels (A) and (B)), the side screw hole 374b is also defined by two holes having the same dimensions as that of the top screw holes 374a. In the covering piece 114 (shown in subpanels (C) and (D)), the side screw hole 374b includes the two holes recessed in a rectangular base hole 378, in this design, having dimensions of 7.5 mm×5.5 mm with a depth of 1.25 mm.

FIGS. 3H-3K show views of the set screws 370 for the top and the side holes. Each set screw 370 includes a screw base 380, two screw pegs 372, and a dissected cylindrical screw 386 with helical threads 388. FIGS. 3H and 3I shows the top center screw holes 374, and FIGS. 3J and 3K show the side screw holes 370b.

In FIGS. 3H and 3I (top screw), the screw 370a includes a screw base 380a that has a contoured base surface 382a matching that of the corresponding cover inner surface 320 in which it sits. Two screw pegs 372 are connected to an underside surface 384 of the screw base 380 in which the contoured base surface 382 is opposite and spaced apart from the underside surface 384. The two screw pegs 372 each extends away from and are substantially perpendicular to the underside surface 384. The two screw pegs 372 include a section with helical threads 388 to mate with a screw cap 376. The dissection of the dissected cylindrical screw 386 forms the two rectangular screw pegs 372 to be extended through the screw holes 372 in the base frame 112 and the covering piece 114. The dissected cylindrical screw 386 is chamfered at the front edge.

The screw base 380, in this design, is 7.5 mm×5.5 mm (as shown in subpanel (B) of FIG. 3I) to fit frictionally in the base hole 378 on the covering piece 114 with a gap of 2 mm. The two rectangular screw pegs 372 are each 4.75 mm×2.25 mm to fit smoothly through the two screw holes 372 and extends with a length of 11 mm (as shown in subpanel (C) of FIG. 3I). The dissected cylindrical screw 386 has a diameter of 6 mm (as shown in subpanel (A) of FIG. 3I) with a helical pitch of 1 mm in five turns; the helix pipe diameter is 0.5 mm.

FIGS. 3J and 3K (side screw) shows an embodiment of the set screws 370 designed for the side screw holes 370b. The screw base 380b on the side of the frame 110 includes a flat surface matching that of the corresponding inner cover surface in which it sits. Most elements and example dimensions are the same as the top center set screw embodiment (as shown in subpanels (A) and (B) of FIG. 3K), except the screw base has a thickness of 1.25 mm (as shown in subpanel (C) of FIG. 3K).

FIGS. 3L and 3M (screw cap) shows an embodiment of the screw cap 376 designed for coupling to the set screws 370. The screw cap 376 includes an inner cap surface 390 with helical threads 392 configured to mate with corresponding helical threads 388 in the set screw 370. The outer cap surface 394 is shaped as a truncated cone having a wide end 396 and a narrow end 398. The wide end 396 helps to hold the breathable filter 120 in place when the screw cap 376 engages with the set screws 370. The breathable filter 120 is secured between the frame 110 and the screw cap 376. More specific dimensions of the screw cap 376 are shown in subpanels (A), (B), and (C) of FIG. 3M.

FIGS. 3N, 3O, 3P, and 3Q (frame hooks) illustrate fastening hooks 900 disposed on the base frame 112. Multiple fastening hooks 900 are shown placed along the second base surface 316 of the base frame 112 between the zygomatic and jaw side point (marked D2). A user can choose specific fastening hooks 900 to engage with fastening straps (not shown) to ensure the optimal fit of the respiratory protective device 102. In FIG. 3N, the dimensions of fastening hook 900 are shown with the hook configured as a hollow squared box shape with rounded edges. In this embodiment, the outer square edge is 10 mm with a corner radius of 1 mm, while the inner square edge is 6 mm with a corner radius of 1 mm. The thickness of each fastening hook 900 is 6 mm. In FIGS. 3P and 3Q, the fastening hooks 900 are shown as implemented on the frame. To place the hooks, as shown in FIG. 3Q, from the zygomatic (8), the midpoint "H1" (center of the first fastening hook 901) is identified for the second base surface 316. The fastening hooks 900, in this design, are placed 12 mm apart (center-to-center) and aligned along second base surface 316. The fastening hooks 900 are repeated until the jaw side point "D2" region.

FIGS. 3R and 3S (frame reinforcement and covering piece assembly) shows the cross-section of the base frame 112 having wing flaps 334 at the connection between the base frame 112 (as shown in subpanel (A) of FIG. 3R) and covering piece 114 (shown in FIG. 3S) to provide frame reinforcement at that section and to retain the covering piece 114. The wing flaps 334 include an extension that extends on both sides of the base frame 112 from the edges 315, 317 of the first and second base surface 314, 316. The wing flaps 334, in this design, have an extending region of 3 mm and a thickness of 1 mm thickness adjacent to the edges 315, 317, as shown in subpanel (B) of FIG. 3R. The wing flaps 334 tapers to a wing flap end 336 to form a wedge shape. The result is a flexible wedge shape that can secure the covering piece 114 within the base frame 112 to form the complete frame 110, as shown in the cross section of FIG. 3S, subpanel (B).

Example Sensor-Integrated Respiratory Protective Device #2

FIG. 3T shows a second embodiment of the frame 111 configured as a unitary structure. In this configuration, the sensor network 103 and conduit 118 may be embedded into the frame 111 during manufacturing (e.g., by 3D printing and/or copper circuit board printing methods). The wiring may be formed using conventional wiring or with printed conductive paint.

Figure 4:
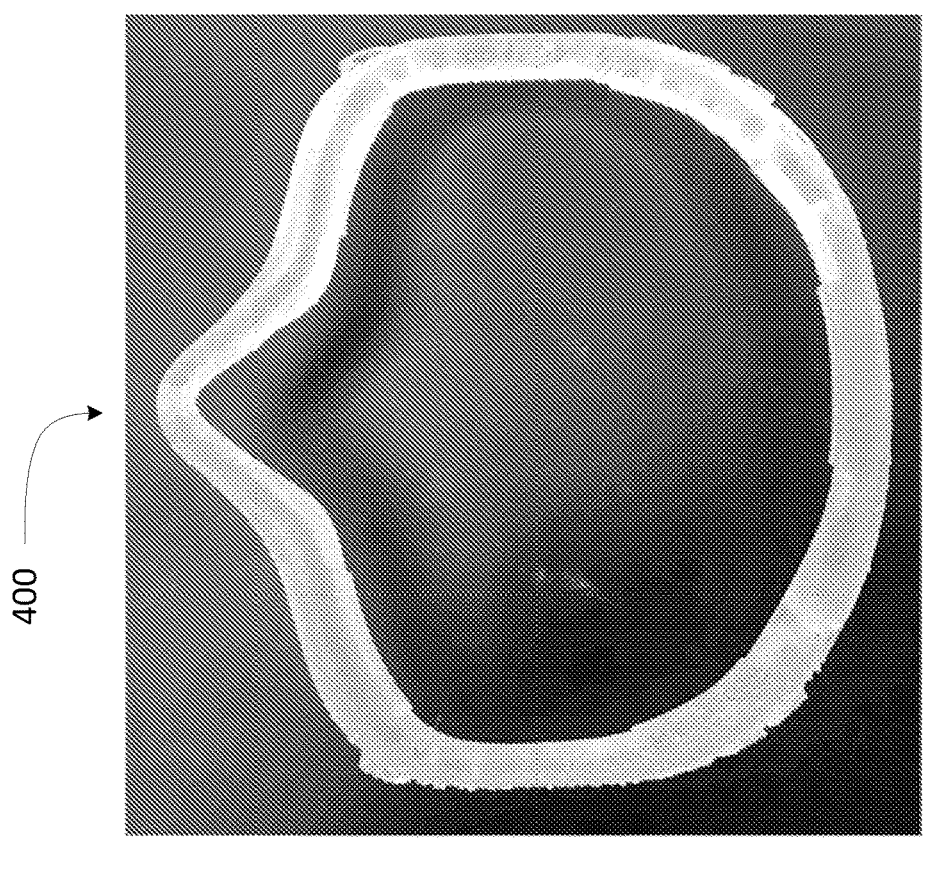
FIG. 4 shows a physical prototype of a respiratory protective device according to one implementation.
Figure 4:
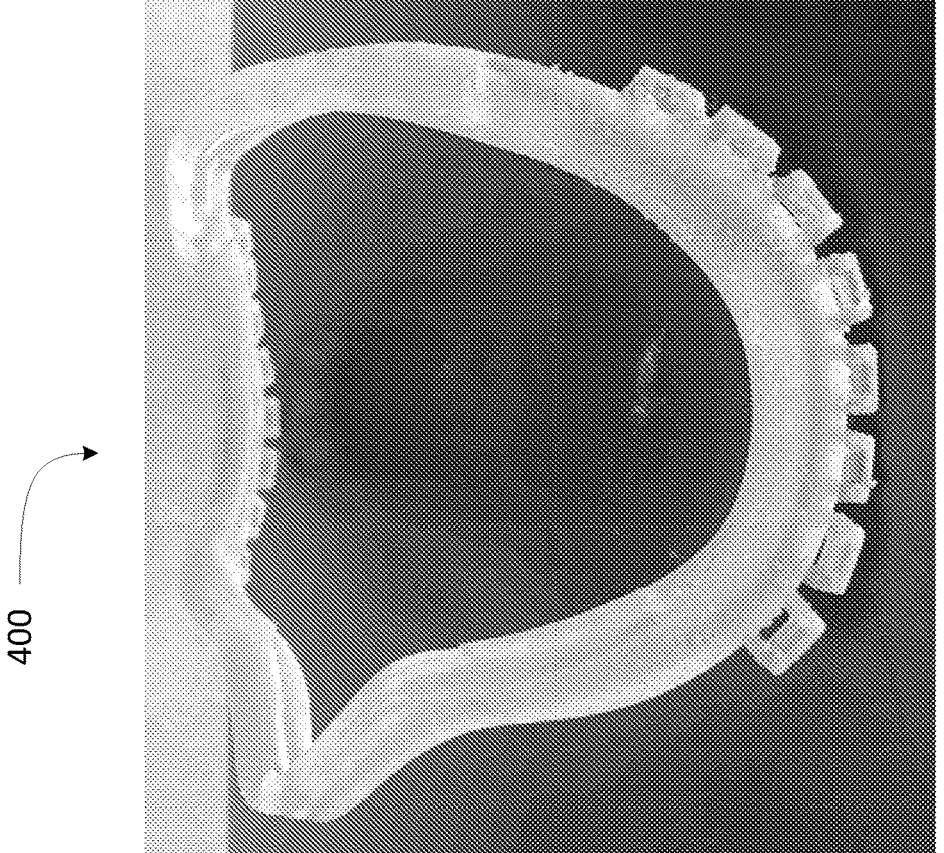

FIG. 4 shows a fabricated prototype of the custom-fit respiratory protective device 102b. The FIG. 4 model frame 400 was printed using Elastic 50A material on Form 3 printers from Formlabs. In other implementations, the respiratory protective device 102 could be conventionally manufactured (e.g., injection molding).

Example Method of Customization and Development

FIGS. 5A-5H illustrate an example method 500 to generate a customized respiratory protective device 102 from a model having a customized frame determined from predefined facial anthropometrical and anatomical landmarks that are adjusted for a specific user, e.g., based on the user's measured scan or measurement.

Figure 5A:
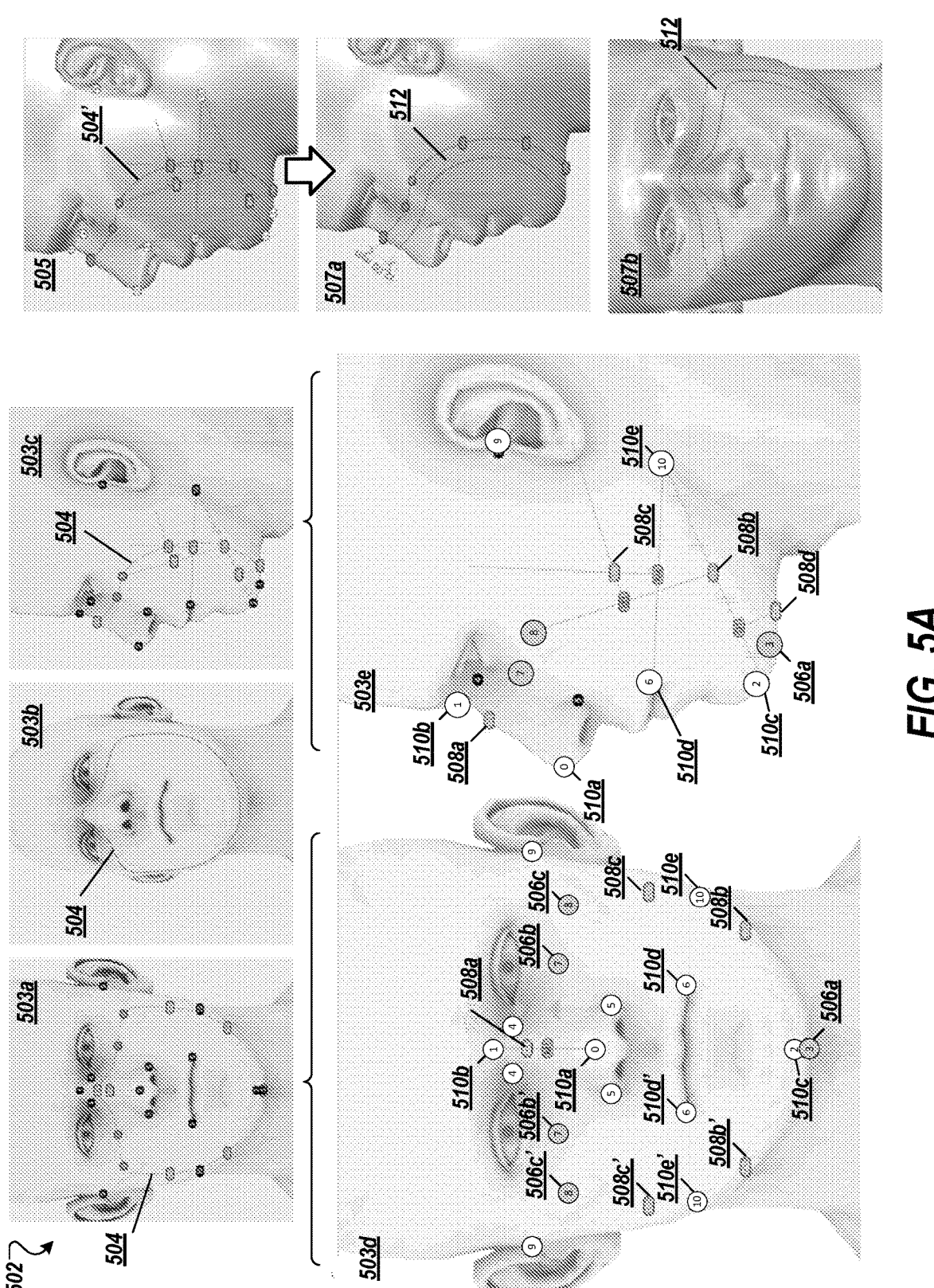
Figure 5B:
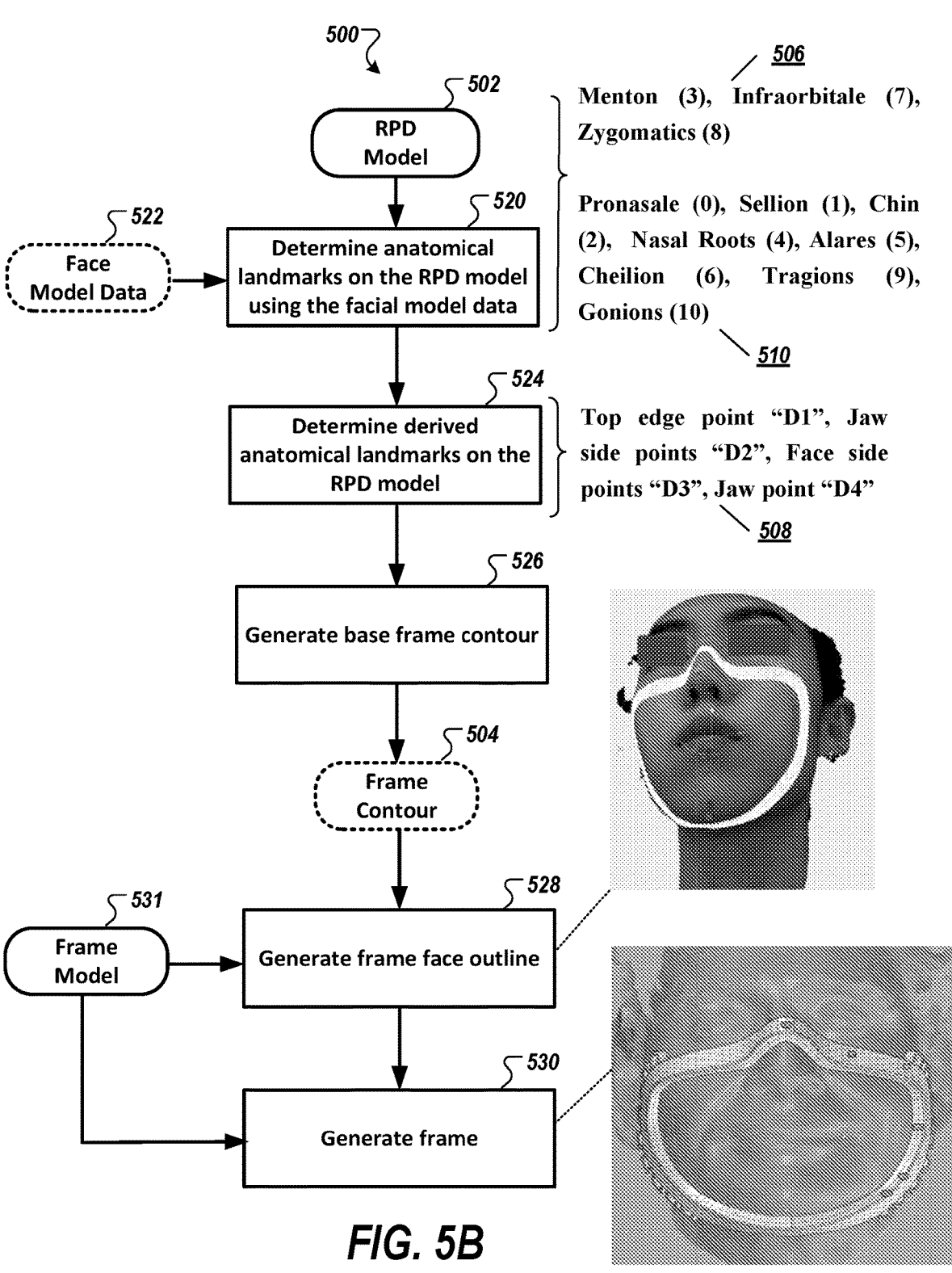

FIG. 5A shows landmarks within a respiratory protective device model 502 that defines a facial contour 504 (see diagrams 503a, 503b, 503c) for a respiratory protective device (e.g., 102). The facial contour 504 defines a base outline of the respiratory protective device and is defined by a set of anatomical landmarks 506 (shown as landmark "3" 506a, landmark "7" 506b and 506b', and landmark "8" 506c and 506c', see diagrams 503d, 503e) and landmarks 508 (shown as the derived landmark "D1" 508a, derived landmark "D2" 508b and 508b', derived landmark "D3" 508c and 508c', and derived landmark "D4" 508d, see diagrams 503d, 503e) derived from other anatomical landmarks 510 (shown as landmarks "0" (510a), "1" (510b), "2" (510c), "6" (510d and 510d'), "10" (510e)). The base outline of contour 504 (shown as 504' in diagram 505) can be expanded to generate the frame outline 512 (shown in diagrams 507a and 507b). FIG. 5B shows an example method 500 to generate the facial contour 504 for the facial model 502. FIG. 5C shows example parameters for the dimensions of the landmarks in the respiratory protective device model 502.

Table 1 provides a list of the landmarks in the respiratory protective device model 502.

TABLE 1

| Contour Landmark | Anthropometrical and anatomical information usage | Description |
|---|---|---|
| Top edge point "D1" (508a) | Derived from Pronasale (point 0) and Sellion (point 1) | Determine from an offset of a midpoint "M1" between Pronasale (point 0) and Sellion (point 1) |
| Jaw side points "D2" (508b and 508b') | Derived from Chin (point 2) and Gonions (point 10) | Determine as a midpoint between Chin (point 2) and Gonions (point 10) |
| Face side points "D3" (508c and 508c') | Derived from Zygomatics Landmark "8," derived Landmark "D2," Cheilion (point 6), and Gonions (10) | Determine as an intersection of (i) a first line projecting from a midpoint "M2" between Zygomatics Landmark "8" and derived Landmark "D2" (ii) a second line projecting from a midpoint "M3" between Cheilion (point 6) and Gonions (10) |
| Jaw point "D4" (508e and 508e') | Derived from Chin (2) and Derived Landmark "D2" | Determine as a midpoint "M4" between Chin (point 2) and Derived Landmark "D2" |
| Menton Landmark "3" (506a) | Derived from Menton (3) | Determine as Menton (point 3) |
| Infraorbitale Landmark "7" (506b and 506b') | Derived from Infraorbitale (7) | Determine as Infraorbitale (point 7) |
| Zygomatics Landmark "8" (50cb and 508c') | Derived from Zygomatics (8) | Determine as Zygomatics (point 8) |

FIG. 5B shows an example method 500 to generate the facial contour 504 for the facial model 502.

Method 500 includes applying an RPD model 502 to face model data 522 of a person. In instances in which the face model data is for a specific person, the resulting RPD is thus designed and customized for that person. In instances in which one or more general face models are employed, e.g., for different sizes and shapes, the RPDs are designed and customized to those models. An example process of acquiring a facial scan is provided in [4], which is incorporated by reference herein.

In some embodiments, the customization and fitting may be described in instructions to allow a person to determine the locations of the Menton (landmark "3" 506a), Infraorbitale (landmark "7" 506b), Zygomatics (landmark "8" 506c), Pronasale (landmark "0" 510a), Sellion (landmark "1" 510b), Chin (landmark "2" 510c), Nasal Roots (landmark "4"), Alares (landmark "5"), Cheilion (landmark "6" 510d), Tragions (landmark "9"), and Gonions (landmark "10" 510e). The person can employ measurements to select a pre-fabricated RPD having similar measurements, e.g., within 1%, within 5%, or within 10%.

In operation 520, the face model data (e.g., a 3D model of a person's face, e.g., cloud, mesh, or geometric data) can be evaluated for a set of pre-defined landmarks, including the Menton (landmark "3" 506a), Infraorbitale (landmark "7" 506b), Zygomatics (landmark "8" 506c), Pronasale (landmark "0" 510a), Sellion (landmark "1" 510b), Chin (landmark "2" 510c), Nasal Roots (landmark "4"), Alares (landmark "5"), Cheilion (landmark "6" 510d), Tragions (landmark "9"), and Gonions (landmark "10" 510e). The operation may be performed by manually marking a person's face with the above-noted landmarks, capturing an image or 3D scan of the face, and importing the digital image or 3D scan into a 3D software. An example of a 3D scanner is the 3dMD system [14]. The scanner can capture a three-dimensional face image, e.g., ear to ear. The data may be stored as a point cloud, geometric mesh, triangular, or polygonal elements or framework. CAD software are available that can import scanned data and construct a 3D model. An example of the CAD software is Rhino CAD software.

The operation may also be alternatively performed using 3D face recognition technology. FIG. 5C shows example parameters for the dimensions of the landmarks in the respiratory protective device model 502.

Method 500 then includes determining (524) derived anatomical landmarks on the RPD model, e.g., the top edge point "D1" (508a), Jaw side points "D2" (508b, 508b'), Face side points "D3" (508c, 508c'), Jaw point "D4" (508d, 508d') as described in relation to FIG. 5A. In some embodiments, the method 500 may determine other derived landmarks for various landmarks described herein, e.g., 506b, 506c.

Top Edge Point Landmark "D1" (508a): To identify the location for the top edge point 508a of the frame, in the example shown in FIG. 5D, diagram 532, the system may employ the Pronasale (point "0" 510a, as the nose height) and Sellion (point "1" 510b) and determine the midpoint "M1" 533 between them (e.g., in the 3D model or with a 2D projection of the model). Based on existing FFR placement data, the average point of the top edge of the FFR is at 57% from the pronasale on the seillion-pronasale line. To accommodate the sensor network for continuous fit monitoring, the system may increment the midpoint "M1" 533 with a pre-defined length 534, e.g., 10 mm for the frame.

Jaw side points "D2" (508b): To ensure that the frame fits well on the side of the face with no leakage, it is observed that the frame should have a smooth contour near the jaw and the sides of the face. In the example shown in FIG. 5D, diagram 536, the pair of jaw side points between the chin point "2" 510c and gonion "10" 510e is determined (e.g., in the 3D model or with a 2D projection of the model) as a midpoint between them.

Face side points "D3" (508c): To ensure a proper fit and a smooth contour on the side of the face with a lot of soft tissue, it is observed that the frame should have one or more "intermediate" points among landmarks along the side of the side. In the example shown in FIG. 5D, diagram 538, the face side points "D3" 530c is determined (e.g., in the 3D model or with a 2D projection of the model) as an intersection of (i) a first line 540a perpendicularly projecting from a midpoint "M2" 540b defined between the Zygomatics Landmark point "8" 506c and derived Landmark "D2" 508b (ii) a second line 540c perpendicularly projecting from a midpoint "M3" 540d between Cheilion (point "6" 510d) and Gonions (point "10" 510e).

Jaw point Landmarks "D4" (508d): To ensure the contours of the frame fit well on the face near the Menton (point "3" 506a), in the example shown in FIG. 5D, diagram 536, the jaw point landmark "D4" 508d is determined (e.g., in the 3D model or with a 2D projection of the model) as an intersection of (i) a line 540e perpendicularly projecting from a midpoint "M4" 540f defined between Chin (point "2" 510c) and Derived Landmark "D2" and (ii) a contour 540g of the jaw.

Figure 5D:
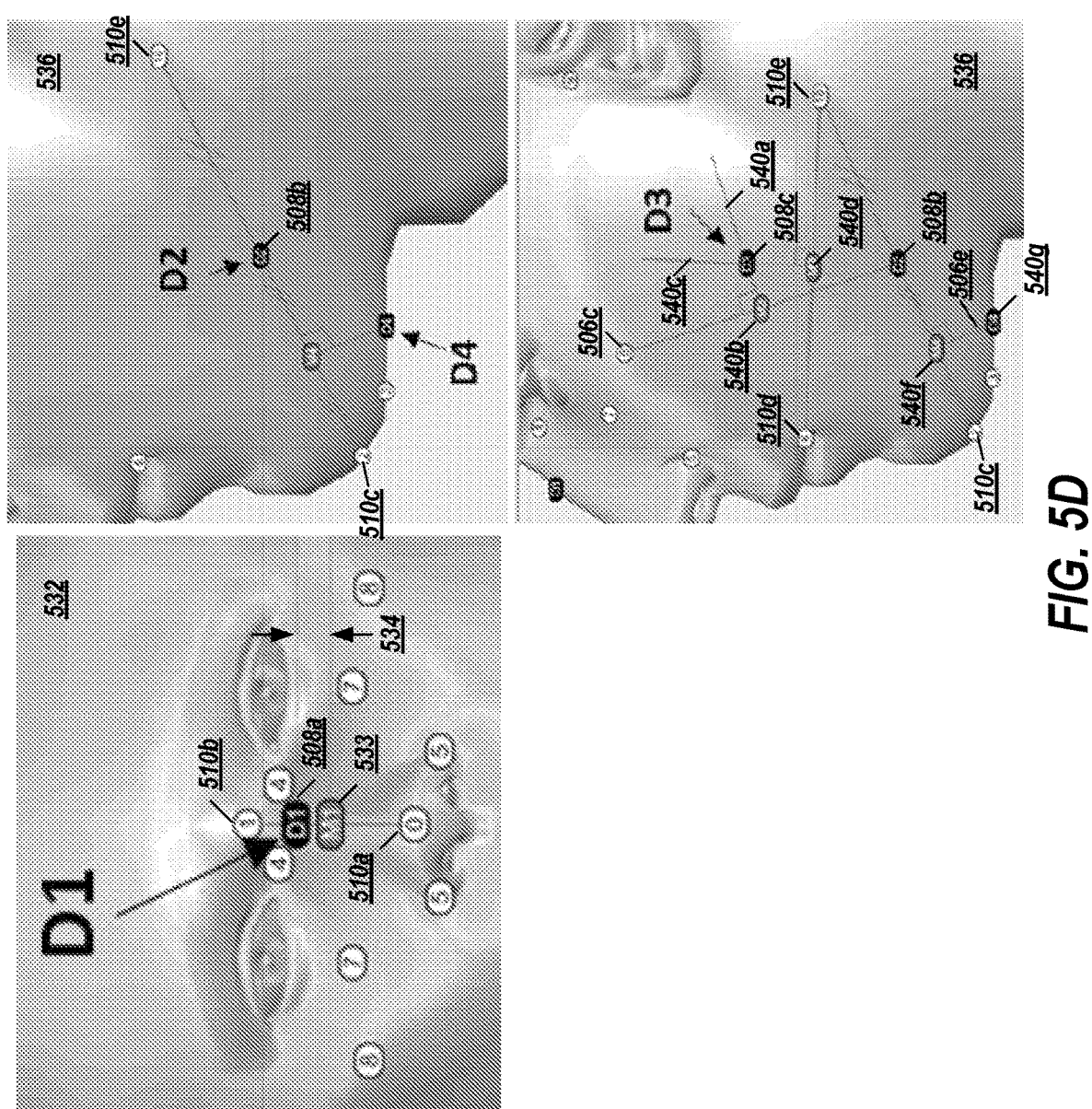
Figure 5E:
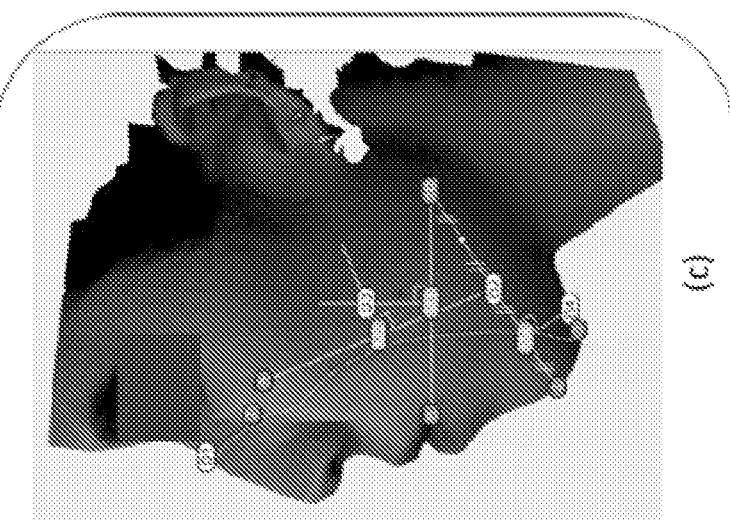
Figure 5E:
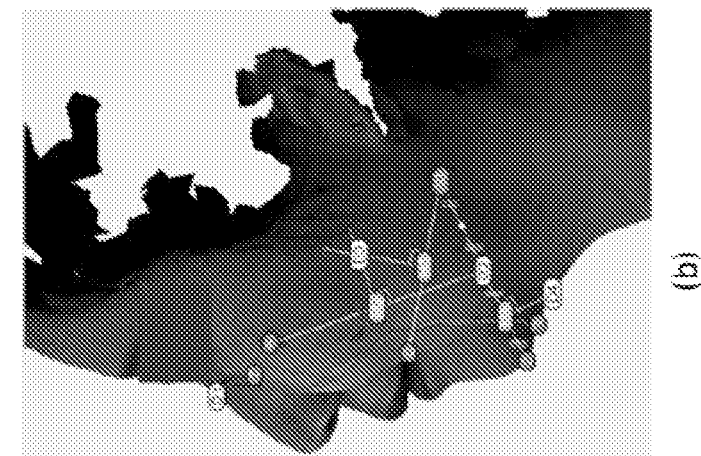
Figure 5E:
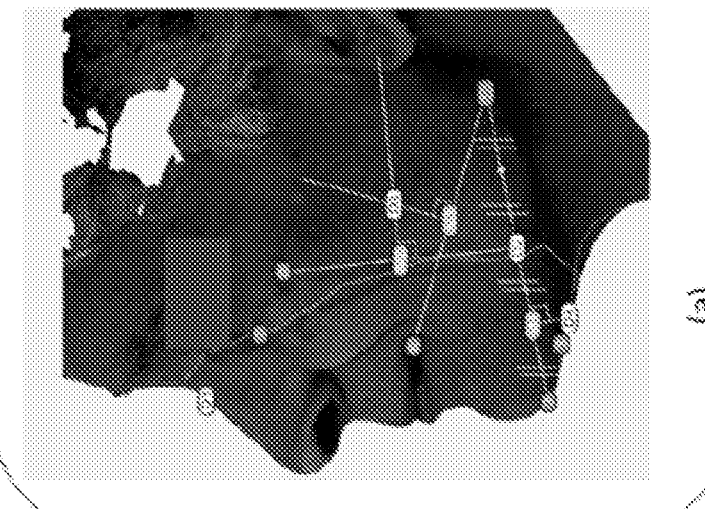

Method 500 then includes generating (526) a base frame contour 504. In some embodiments, the contour is generated by interpolating (e.g., via curvilinear interpolating or other smoothing interpolation) between the defined landmarks, e.g., 508a, 506b, 506c, 508c, 510e, 508b. 506a, 508b', 508c', 506c', 506b'. The operation may be performed (i) for the full face or (ii) for half of the face and mirrored for the other half. The contour is then projected onto the scan data with the face shape for each subject. FIG. 5E shows the base frame contour 504 for three different subjects.

In some embodiments, the operation begins with the top edge point (D1) in the side view; interpolation is then performed between the points infraorbitale (7), zygomatic (8), the face side point (D3), the jaw side point (D2), and the jaw point (D4). This is then projected onto the face scan to obtain the frame contour that wraps onto the facial profile.

Method 500 then includes generating (528) a frame face outline 512. In the example shown in FIG. 5A, an offset of 12 mm inwards is made to accommodate the sensor network. It has been determined that 12 mm is the optimum surface width of the respiratory protective device frame to rest well on the face of an adult. Then, a projection of both contours onto the facial profile scan is performed to create the 3D base frame contours. Other offsets may be used.

Method 500 then includes generating (530) the frame 102, further described herein.

Experimental Results and Additional Examples

A study was conducted to design and develop a custom-fit reusable RPD. The developed custom-fit reusable RPD can be customized using facial scanning or facial fitting. The RPD was designed to facilitate easy replacement of the filter and decontamination of the frame after every use. By facilitating the customization of the RPD—ensuring the right fit and choice of the filter with the desired degree of filtration—the custom-fit reusable RPD can be used for adults and children. The study analyzed facial features and anthropometry in the design of the custom-fit RPD.

Selection of Anthropometric Facial Landmarks. The study evaluated human facial anthropometrical data, including anatomic landmarks, dimensions, and contours that define an individual's facial profile in designing a custom-fit RPD. These anthropometric characteristics were used as "references" for customizing the RPD for any facial profile. An initial challenge lies in identifying the right set of these anthropometric facial landmarks. An earlier NIOSH study, which identified 26 pre-defined landmarks and 21 facial dimensions, was used as the starting point for the present study [13]. The present study selected an initial 18 of those 26 facial landmarks that were focused on the lower face (below the nasal root points since the proposed device is analogous to a half-facepiece respirator).

Among these selected landmarks, some are not directly relevant to the purpose of measuring either the face size or the base frame shape but serve as reference points that can help better position and orient the face images in horizontal and vertical planes. For example, the pupils, pronasale, chellions, and tragions can assist with balancing the symmetry for the facial image. The black landmarks in the figure aid in positioning, orienting, centralizing, and symmetrizing the scan data and mappings. The landmarks "3," "7," and "8" fall on the contour of the frame.

In addition to selecting the landmarks, specific dimensions were identified that must be measured to characterize the facial profile. The study employed 15 facial dimensions, six of which are from the NIOSH study's 21 facial dimensions; the others were identified specifically for creating a customized RPD. Eleven of these dimensions were straight-cut distances from point to point. The remaining four dimensions were straight-cut vertical ratio measurements, which, similar to reference landmarks, are reference proportion lines for positioning and orienting. FIG. 5C shows the selected facial landmarks and the various dimensions employed for the design.

3D Scanning and Customized Frame Contour Development: For developing the customized RPD, the study developed a design framework that took a 3D scanned image, put it into a 2D framework for the analysis, which was then projected back to the 3D space for 3D-customized printing of the frame.

The study developed customized RPD for three participants (2 females and 1 male) with different facial profiles. The study used the 3dMD System for scanning the facial profiles [14]. The 3dMD face scanner captured the three-dimensional face image from ear to ear. The system employed manual labeling of the facial anthropometrical and anatomical landmarks. Before scanning, the subject was physically marked with a red lip liner at the facial landmarks 531 shown in FIG. 5C. For the 3D scan, the participants were asked to look straight and relax their facial expressions while the 3D cameras recorded a 10-second footage with over 100 scan frames. The exported files for each participant contained all the frames in an OBJ file format with colored textures. The landmarks were seen clearly on the faces. It was observed that the 10-second footage could provide selectable images from the multiple frames in which the selected image was without blurs or noise due, e.g., due to the inevitable shaking, swinging, or blinking that may occur during the scanning.

The study used 3dMD Vultus, a native software for the 3dMDface™ System, to process the scanned image. The study virtually re-marked in the software the landmarks and measured their dimensions. The study applied different tools (plane cut, mask, and refinement) to cut off the unwanted debris and fragments (e.g., hair texture) to focus on the front face area. The core task was to use the measurement and analysis tools to digitize the landmarks and dimensions.

Figure 6A:
FIGS. 6A-6F show various aspects of a study conducted to develop a customized respiratory protective device.

The study developed landmark and dimension analysis scripts to analyze the scanned profiles of the subjects for the landmarks and dimensions. With the available landmark and analysis (dimension) scripts, the points were overlaid onto the physical landmarks and placed marks onto the non-contactable landmarks (e.g., pupils). In the built-in world coordinate system, each landmark had a coordinate (x, y, z), and the origin (0, 0, 0) was placed at the pronasale point as the center reference point on the face. The other landmarks were accordingly updated to their new coordinates. This helped to understand the overall relationship between all the landmarks easily and quickly. Subsequently, the analysis script automatically generated a report file for all the dimensions measurements needed. FIG. 6A shows the scanned images of one of the participants in 3dMD's Vultus program.

A Taxonomy of Landmarks: A study proposed taxonomy for the set of facial landmarks for developing the custom-fit RPD. As shown in the chart illustrated in FIG. 6B, the defined landmarks are those obtained from literature and serve as the basis for identifying additional landmarks for developing the contour of the RPD frame. These defined landmarks were classified into guiding landmarks and construction landmarks. The guiding landmarks guide the design of the customized frame; for example, pronasale (0) served as the origin (0, 0, 0) for the computations. The construction landmarks were used for constructing the final contour of the frame. The various intermediate landmarks that served to develop the final set of landmarks—based on geometrical relationships with the defined landmarks—were called process landmarks. These process landmarks were used to derive the derived landmarks. Thus, the customized frame contour was constructed using the construction landmarks and derived landmarks.

This taxonomy has a critical role to play in designing and developing a custom-fit RPD to fit any facial profile. The derived landmarks were based on defined steps (algorithms) drawing upon the defined landmarks as the foundation. Therefore, the process of creating a customized contour for any facial profile can be automated using the algorithms underlying the taxonomy shown in the figure. FIG. 6C shows the locations of the various facial landmarks in the taxonomy.

Defining a Taxonomy of Landmarks. The study imported the textured scanned data into Rhino® CAD software to construct the 3D model of the RPD frame. With the pronasale point as the origin of the coordinate system, the study mapped out the other landmarks by placing the exact three-dimensional coordinates in the Rhino software coordinate system. The first step in the "3D to 2D to 3D" design methodology is "3D to 2D. The study performed a geometrical projection of all the three-dimensional landmarks onto a two-dimensional plane that is parallel to the coronal plane to provide 2D mapping that employs all the landmarks with their relationships in lateral (horizontal or Y-axis) and medial (vertical or Z-axis) directions.

The study then augmented the chosen facial landmarks in FIG. 5C with landmarks on the side of the face and the jaw area for drawing a smooth contour of the RPD frame. The "3D to 2D to 3D" design framework was followed to project all the pre-defined physical landmarks onto both the front view 2D plane and the right-side view 2D plane. This provided a better understanding of the numerical and geometrical relationships of the landmarks and facilitated the identification of new ones for drawing the smooth contour of the RPD frame. This initial set of landmarks, termed "Defined Landmarks," did not provide a smooth contour of the entire RPD frame. Therefore, the study developed algorithms to identify new landmarks on the front view 2D mapping. These new landmarks are "derived" based on the Defined Landmarks and are named "Derived Landmarks."

Derived Landmarks: One of the challenges during the use of FFRs is the interference of the top edge of the device with users wearing eyeglasses. Consequently, the use of sellion or nasal root as one of the landmarks for defining the contour of the RPD frame would not be appropriate as they could cause interference. To identify the right location for the landmark for the top edge of the frame, the straight-cut distance was measured from the sellion to the pronasale (termed nose height) for the three subjects.

The study evaluated the subjects. The three subjects wore FFRs (the Cup and Duckbill models) to find out where the top edge of the FFRs fell on the sellion-pronasale line. The average point of the top edge of the FFR for the three subjects was at 57% from the pronasale on the seillion-pronasale line. To accommodate the sensor network for continuous fit monitoring, a 10 mm width was allocated for the RPD frame. Therefore, the location selected at one-half nose height is the inner edge of the frame. This means the midpoint of the sellion-pronasale line must be offset upward by 10 mm to locate the top vertex of the outer frame edge. FIG. 5D shows the steps for arriving at D1, the top edge point for the contour of the frame. As seen in the figure, the algorithm utilizes the Defined Landmarks of pronasale and sellion as the foundation to identify D1, the Derived Landmark.

In the study, to determine the top edge point, a straight line was drawn between the pronasale (0) and sellion (1), e.g., as shown in FIG. 5D, diagram 532. The midpoint of line 0-1 was determined and marked as "M1.' The M1 point was then offsetted by 10 mm (for the three adult participants) upwards along the line 0-1 and marked as "D1".

To determine the jaw side point "D2", a straight line was drawn between chin (2) and gonion (10), as shown in FIG. 5D, diagram 536. The midpoint of line 2-10 was determined and was established as the "D2" point.

To determine the face side point "D3", a straight line was drawn between zygomatic (8) and "D2." The midpoint of line 8-D2 was determined and was established as the midpoint "M2". A second straight line was drawn between chellion (6) and gonion (10). The midpoint of line 6-10 was determined and was established as the midpoint "M3". Perpendicular lines were then drawn at each of the midpoints "M2" and "M3". Lastly, an intersection point of the two perpendicular lines was determined and marked as "M3".

To determine the jaw point "D4", the midpoint of line 2-D2 was determined and marked as "D4". A perpendicular line was then drawn from "M4" until it intersected the jaw; the intersection is labeled as "D4".

Developing the RPD Frame Contour: Using the defined Landmarks and the derived landmarks, the study established the contour of the RPD frame by interpolating (curvilinear) between the points. The study then projected the contour onto the scan data with the face shape for each subject. The frame contours for the three subjects were smooth. However, the need to provide a surface, say 10 mm wide, for the frame to rest and fit well on the face made it harder to extend the frame near the Menton (3)—one of the Defined Landmarks. Therefore, after a series of iterations, the study calculated the new derived landmark (D4) to replace the Menton, as described in relation to FIG. 5D. FIG. 5E shows the four Derived Landmarks on the digital scans of the three subjects by following the algorithms in FIG. 5E.

Realization of RPD Frame: FIG. 5A, particularly diagrams 503a, 503b, and 503c, shows the realization of the RPD frame contour using the landmarks defined in the taxonomy. Beginning with the top edge point (D1) in the side view, the study interpolated between the points infra-orbitale (7), zygomatic (8), the face side point (D3), the jaw side point (D2), and the jaw point (D4). Then, this is projected onto the face scan to obtain the frame contour that wraps onto the facial profile.

Figure 6B:
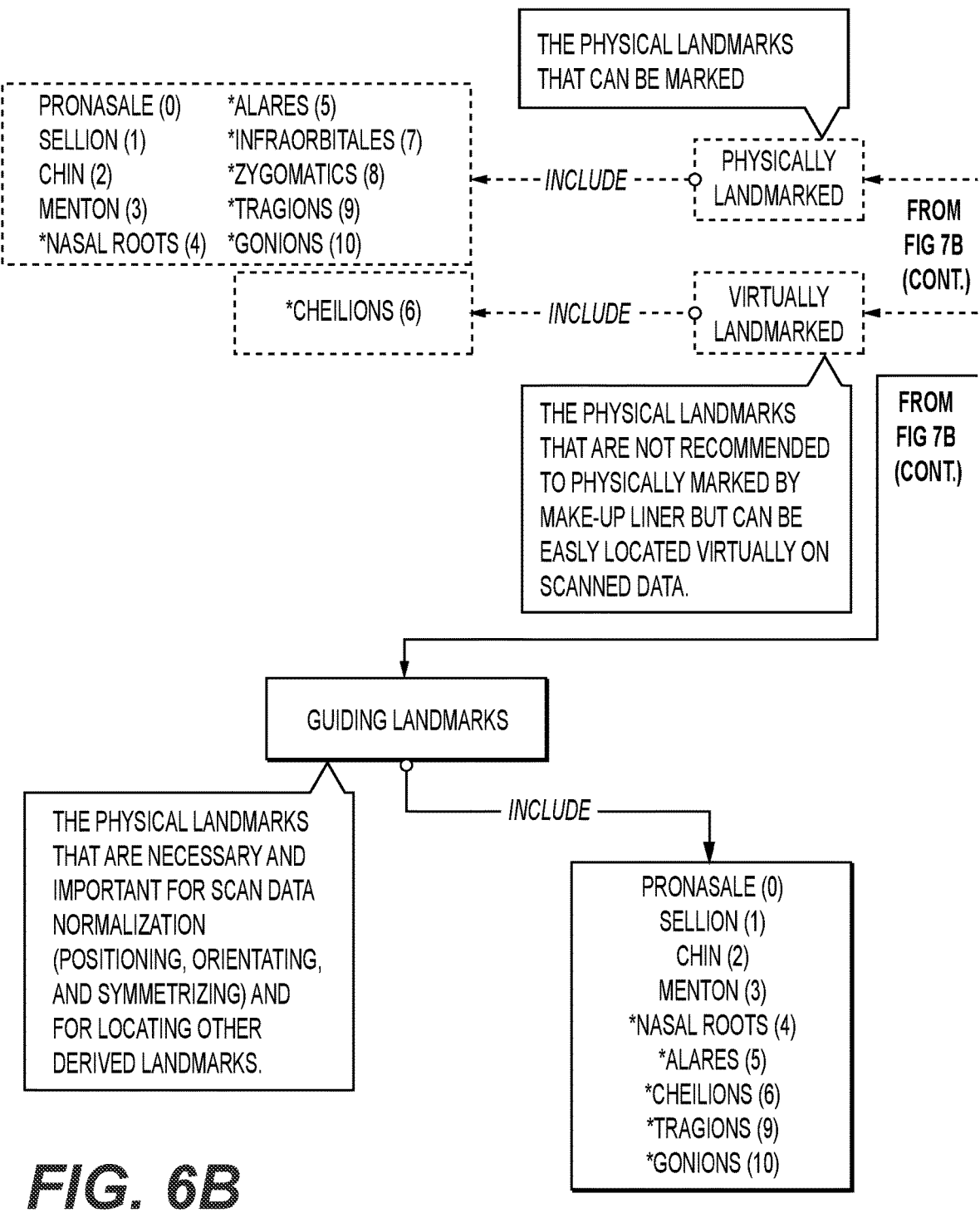
Figure 6B:
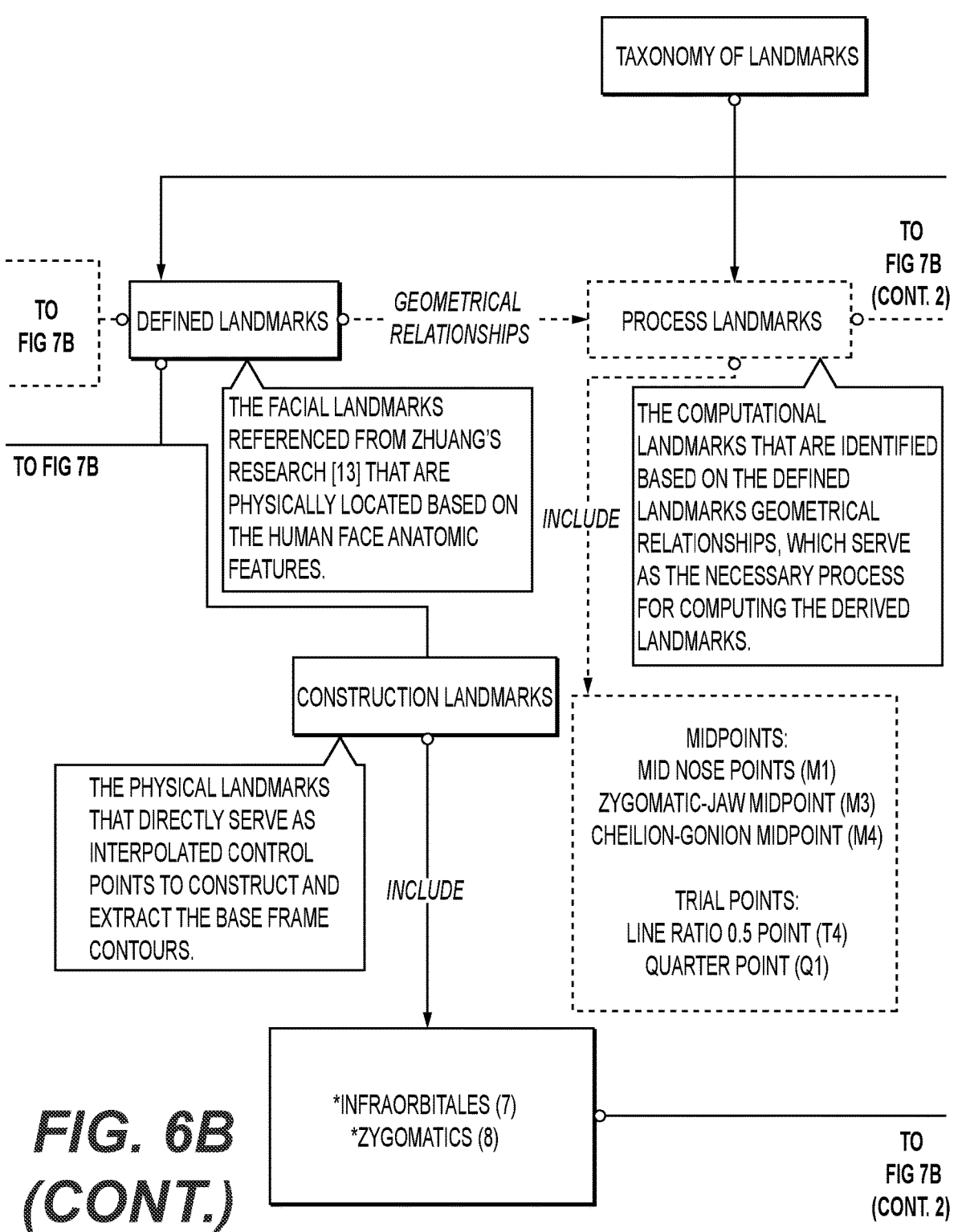
Figure 6C:
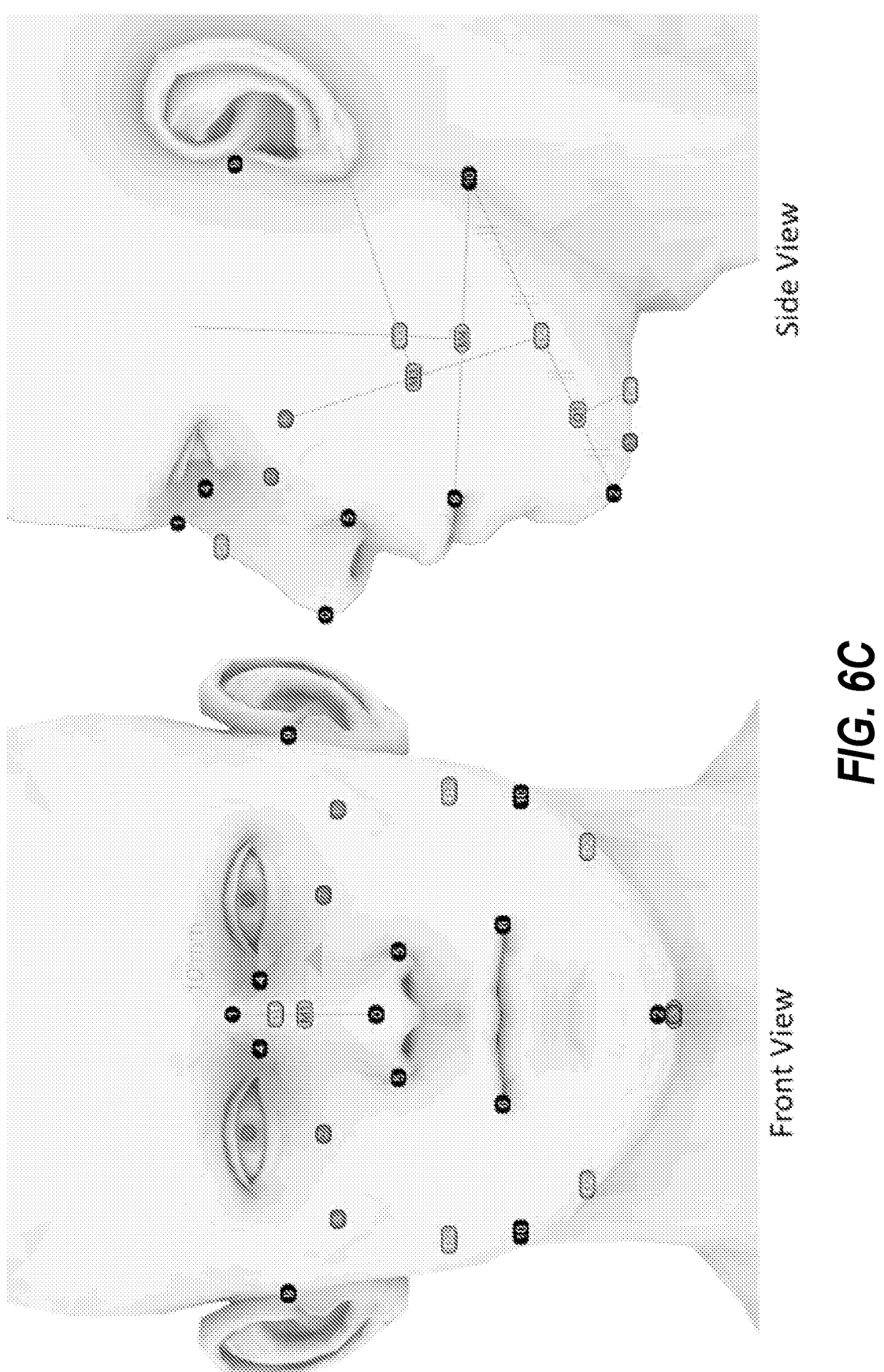
Figure 6D:
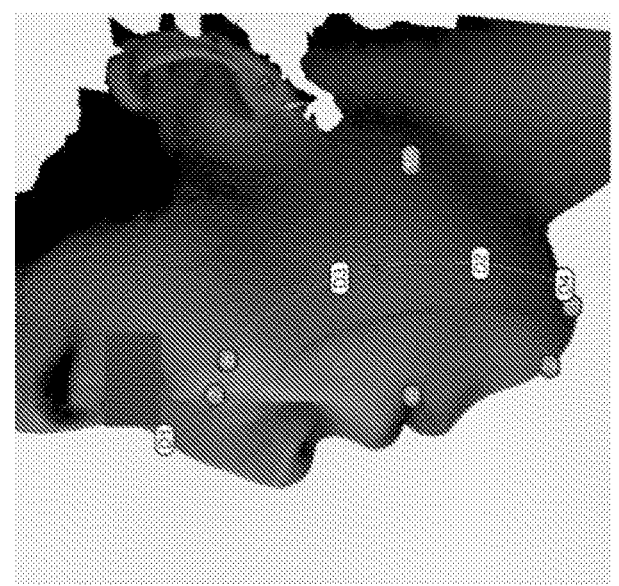
Figure 6D:
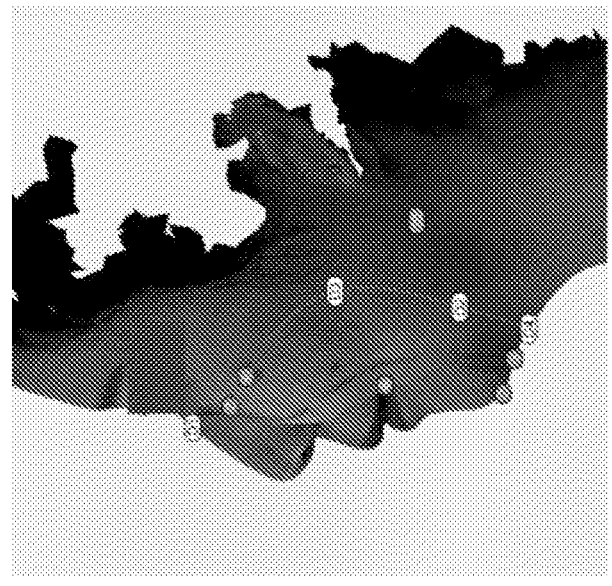
Figure 6D:
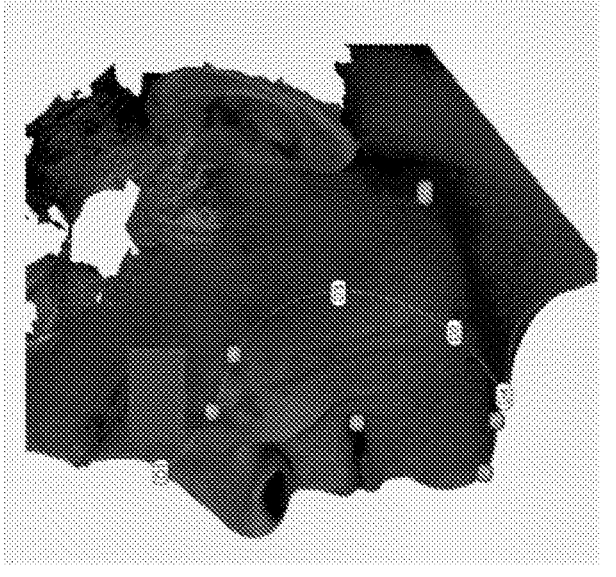

Thus, the methodology utilizing the set of landmarks in FIG. 6B led to the transformation of a scanned digital image of an individual's facial profile to a custom-fit digital prototype of the RPD frame. The realization of custom-fit digital frames for three subjects with different facial profiles validated the algorithms and the robustness of the methodology. The realization of the facial profiles can be seen on three different subjects in FIG. 6D.

From Frame Contour to Frame Surface: FIGS. 5A and 5B show the steps to create the surface from the initial contour derived from the landmarks. Through multiple iterations during which the frame width was changed, 12 mm was determined as being the optimum surface width of the RPD frame to rest well on the face. FIG. 5B also shows the digital RPD Frame with the surface for one of the subjects.

FIG. 3B shows the profile and principal dimensions of the RPD Frame, which has an overall thickness of 8 mm. To reduce the weight and footprint of the RPD around the nose bridge area, the thickness of the Frame was reduced from 8 mm to 7 mm from the infraorbitale (7) to the center of the nose bridge on either side. Likewise, the wall depth was reduced from 4 mm to 3 mm.

Figure 6E:
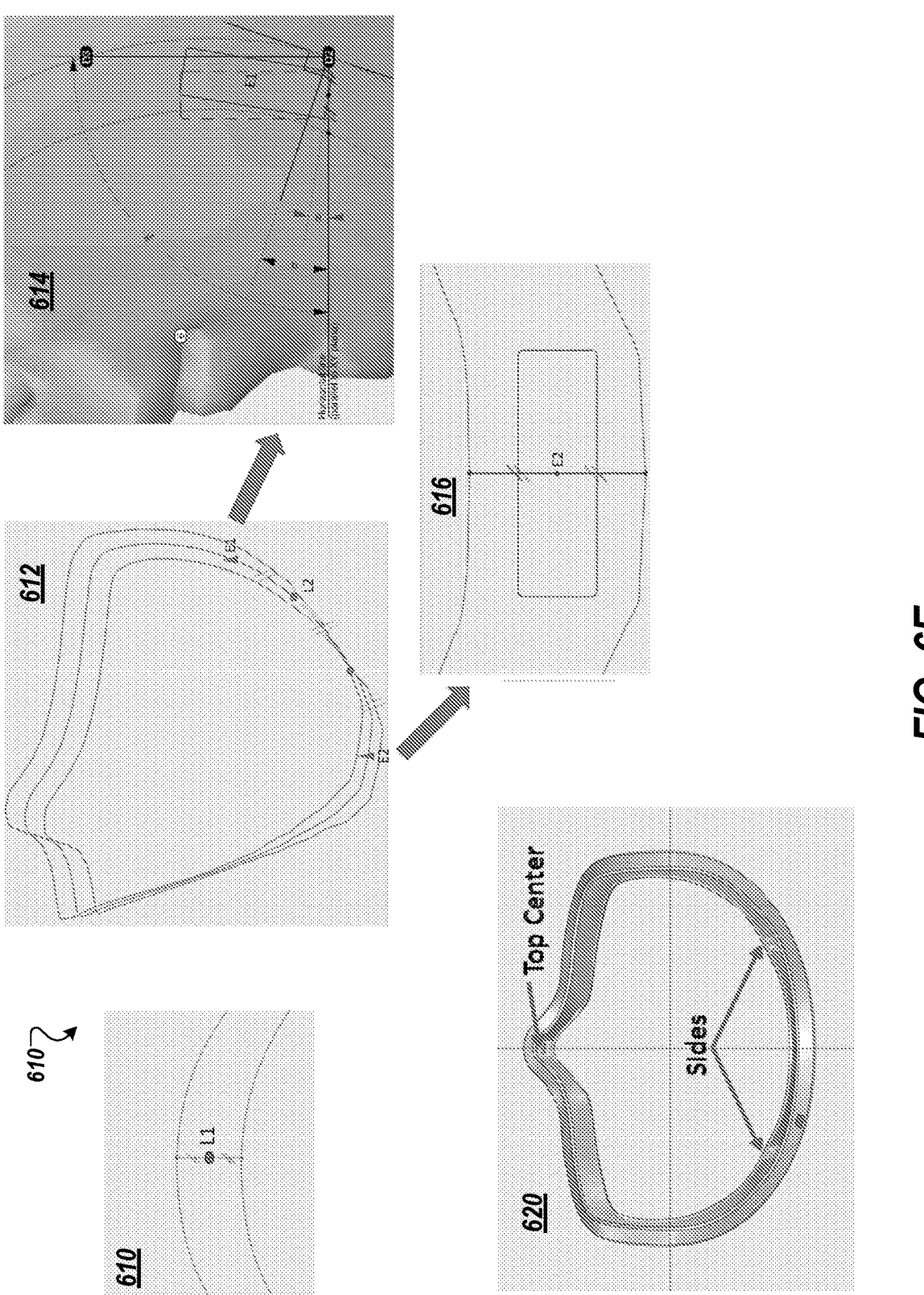

Mechanism for Holding the Filter during Use. The study designed means to secure the filter in the RPD frame during its use using a screw peg and screw cap. This functionality would help realize the ability to use a filter of the desired filtration efficiency, discard it after use, and decontaminate the RPD frame. The screw peg would pass through the holes designed in the frame. The filter would be inserted into this peg, which would be held in position by the screw cap. Three locations were identified where the filter would be held securely during use: One at the top center and one on either side of the frame. FIG. 6E depicts the process for obtaining each of these locations.

FIG. 6E, diagram 610, shows the process for locating the top hole in the frame for inserting the screw peg and topping it with a cap to secure the filter in the frame. For the top hole, a line can be constructed between the inner and outer frame contours at the top center. The midpoint of that line may be found and marked "L1". The line L1 would be the center point of the interlocking holes on top.

FIG. 6E, diagrams 612 and 616, show the steps in locating the bottom point E2. A line can be constructed at the bottom center between the inner and outer frame contours. The midpoint of that line can be marked as point "E2".

FIG. 6E, diagrams 612 and 614, show the steps in locating the side opening for the screw set to hold the filter securely. From the derived landmark "D2", a horizontal line can be constructed in the X-Y plane until it intersects the inner frame contour. The midpoint of this line segment can be determined between the two contours. A 25 mm×8 mm rectangle can be constructed using the midpoint as the bottom edge center in the vertical direction in the X-Y plane (shown in a dotted line). Then, a straight line can be drawn connecting D2 and D3. Next, a tangent can be constructed at "D2" and a perpendicular line at D2 drawn on the inner contour. The angle α can be measured between the horizontal line and the perpendicular line at D2. The angle β can then be measured between the horizontal line at "D2" and the D2-D3 line. Based on the values of α and β, the angle θ can be computed by which the rectangle could be rotated (e.g., if β<90°, θ=0; If β=90°, θ=0.5α; If β>90°, θ=0.9α). Then, the diagonals for the rotated rectangles can be drawn, and the intersection point marked as "E1".

For the interlocking hole locations, a tween curve can be drawn following the frame contours through points "E1" and "E2," as shown in diagram 612 of FIG. 6E. The contour can be divided between "E1" and "E2" into three equal segments. The one-third point from "E1" can be marked as "L2". This would be the center point for the interlocking holes on the side of the RPD frame. For the symmetrical interlocking hole position (L3) on the other side of the frame, the "L2" point can be mirrored around the Z-axis.

Figure 6F:
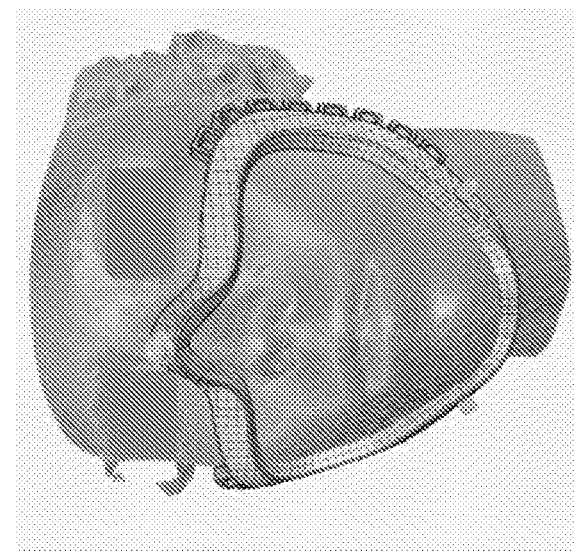
Figure 6F:
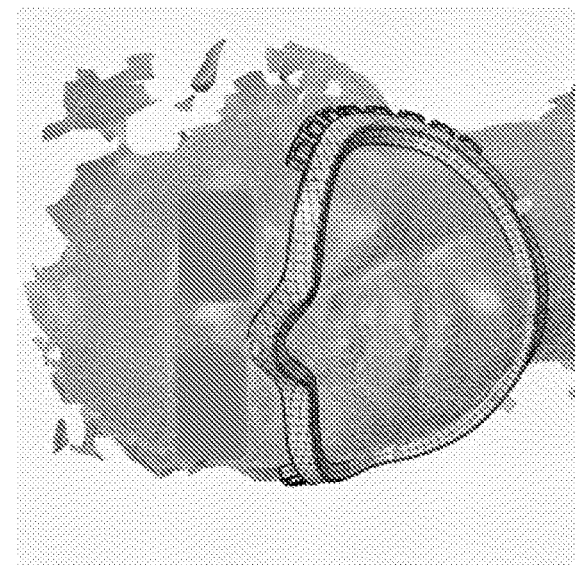
Figure 6F:
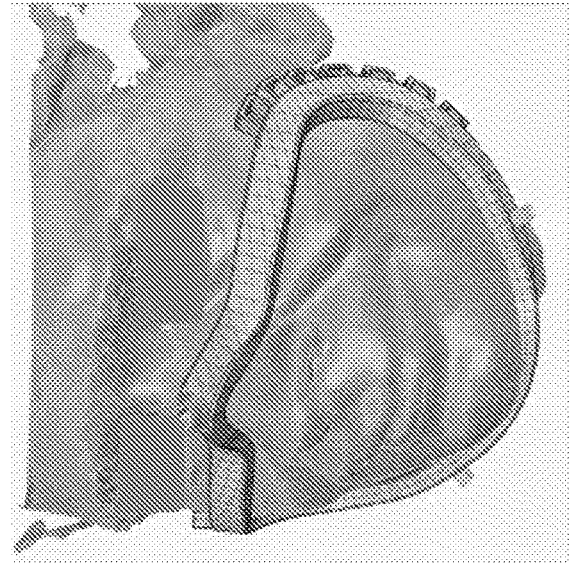

FIG. 6E, diagram 620, shows the digital prototype with the locations of the three screw sets. FIG. 6F shows a finished example of the above experimental process with the digital prototype of a custom-fit RPD with three different frames on the three different subjects.

Evaluation of Responsiveness of Custom Fit RPD to Facial Profile Changes. The study evaluated the responsiveness of the custom-fit RPD to changes in facial profile during use from natural to talking, to smiling, and to yawning. It confirmed that the custom-fit RPD could adapt to such facial profiles.

Figures 6B, 7B:
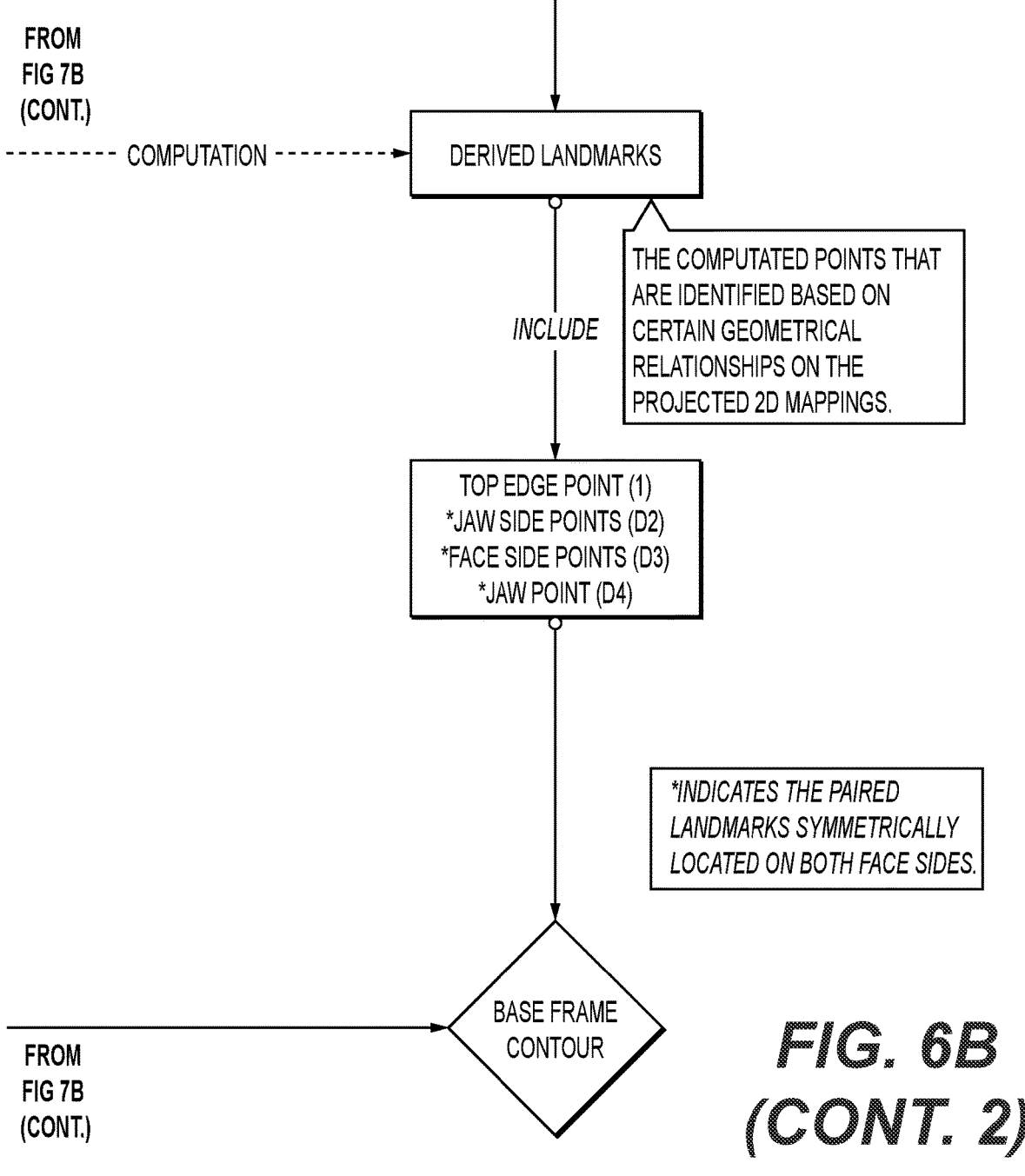
Figure 7:
FIG. 7 shows simulated performance results of the customized respiratory protective device to ensure seal in various facial movements, according to one implementation.

FIG. 7 shows a composite view of the digital scans of the facial profiles of a subject in the four states. The degrees of movement of the key landmarks, viz., Chin (2), Jaw Side Point (D2), and Face Side Point (D3), and the contours of the RPD Frame are shown as solid lines in different colors with changes in facial profiles.

The solid red line 702 in FIG. 7A shows the RPD frame contour in the subject's natural state. In the talking state in FIG. 7B, the degrees of movement of the three landmarks are shown as the facial profile changes from the natural to the talking state. The solid red line (702) and the blue line (704) represent the contours of the RPD Frame in the natural and talking states, respectively. This confirms that the RPD responds to changes in the facial profile and moves with the landmarks, thereby ensuring the integrity of the face seal.

In the smiling state in FIG. 7C, the degrees of movement of the landmarks from the natural to the smiling state are shown along with the contours of the RPD Frame in the natural (red, 702) and smiling states (green, 706), respectively. This once again confirms that the RPD responds to changes in the facial profile and moves with the landmarks, thereby ensuring the integrity of the face seal.

In the yawning state in FIG. 7D, the degree of movement at the chin is significantly greater than that in the other states. The contours of the RPD Frame in the natural and yawning states are also shown in the figure in the solid red (702) and orange lines (708), respectively. This once again confirms that the RPD responds to changes in the facial profile and moves with the landmarks, thereby ensuring the integrity of the face seal.

Material Evaluation and Selection:

The study selected material to create the respiratory protective device frame that effectively balances device fit with comfort. The selected material was also shape-conformable to ensure the frame's structural integrity over repeated use and decontamination. In addition, the selected material materials were 3D-printable. The study reviewed a standard Ashby plot that shows the relationship between density and Young's modulus of various classes of materials [15], as well as the relationship between Young's modulus and tensile strength [16].

The study determined, from the Ashby plot, "elastomers" was the class of materials with the right combination of strength and flexibility that comes close to having the feel, softness, and flexibility of human skin. These characteristics were determined important for the respiratory protective device since its usage over long durations should not cause pressure injuries. The materials in this class include ethylvinyl acetate (EVA), silicones, polyurethanes, neoprene, butyl rubber, and isoprene, among others. Furthermore, silicones fall into the class of flexible polymer foams, potentially making them ideal candidates for the respiratory protective device frame material. These materials may also be responsive to changes in the facial profile of a user during use, including a natural state and one of a talking state, smiling state, and/or yawning state.

Hardness was considered as a property that should be considered in balancing comfort with the fit and hence protection. The study used the Shore Hardness continuum for the various classes of materials to select materials [17]. The study determined the chosen material should be in the range of extra-soft and soft materials with a maximum Shore hardness of 00-60, but preferably up to 00-40. Materials in this "elastomer" hardness range include silicones, isoprene, neoprene, and polyurethane, among others.

Table 2 shows the properties of silicone-based materials, e.g., that can be used for 3D printing of the frame and device components described herein: Elastic 50A [18], SIL30 [19], SILASTIC 3D 3335 LSR [20], and AMSil [21].

TABLE 2

| Manufacturer | Material | Tensile Strength (MPa) | Tear Strength (kN/m) | Elongation @ Break (%) | Shore Hardness (A Class) | Material Type |
|---|---|---|---|---|---|---|
| Formlabs | Elastic 50A | 3.23 | 19.1 | 160 | 50 | Silicone Urethane Elastomer |
| Carbon 3D | SIL 30 | 3.5 | 10 | 350 | 30 | Silicone Urethane Elastomer |
| DOW | SILASTIC 3D 3335LSR | 8.3 | 0.05 | 5.25 | 50 | Liquid Silicone Rubber |
| Elkem | AMSil | 2 | 10 | 200 | 70 | Engineering Silicone |

In evaluating the materials, the study determined the shore hardness to be a property of interest because the respiratory protective device should be soft on the user's face. After a comparative analysis of the properties, the study decided that Elastic 50A and SIL 30 were potential candidates for creating the physical prototypes because their Shore A hardness was in the 30-50 range. Even though the Shore A hardness of Silastic from Dow was 50, its tear strength was only 0.05 kN/m, which was very low compared to the other two materials. Both SIL 30 and Elastic 50A are also compatible with cleaning solvents used for decontamination, including, but not limited to, bleach (NaClO, 5%), Sanitizer (NH4Cl, 10%), or solvents for elastomeric respirators, and UV radiation.

Discussion

Facial Features and Anthropometry. The shape of the human face is complex and diversiform due to a multitude of reasons, including gender, ethnicity, and demographics [22]. Zhuang and Bradtmiller (2005) developed and proposed a fundamental and universal measuring approach for head-and-face anthropometry [13]. This study surveyed the head-and-face anthropometrical measurements among U.S. respirator users, including over 3,997 samples, and covered three major ethnicities in the U.S. (Caucasian, African American, and Hispanic), the majority of age ranges (from 18 to 66), and both genders. The captured head-and-face size distribution among the U.S. population includes 26 landmarks and 21 dimensions. These landmarks and dimensions cover both face size evaluation and head size. These have been valuable for manufacturing filtering facepiece respirators (FFRs) since they can help categorize size ranges and aid in fitting them to users. In their study on fit panels, Zhuang et al. (2008) quantitatively analyzed respirator size fit for different users in terms of pre-defined size ranges [23]. They found outliers and improper fit in small and large size ranges. Lin and Chen (2017) investigated the effect of the FFR style on the fit experience of an Asian population [24]. They used the Cup, Fold, and Liner FFR models, which have distinct edge contours, in the study. Based on the fit panel test and data analysis, they concluded that the Fold model fit significantly better than the other two models for medium and large facial size groups [24]. Therefore, today's practice of producing FFRs in standard sizes based on a grading system limits users' options and leads to challenges with fit and comfort, thereby potentially compromising the degree of protection for users.

A respiratory protective device (RPD) is defined as any personal device that provides protection against inhalation hazards when used effectively, acknowledging that each device may offer either personal protection or source control, or both at varying levels [25]. Jayaraman and Park (2020) proposed the concept of scanning an individual's face to create a custom-fit respiratory protective device (RPD) frame with a replaceable filter of desired protection level (e.g., N95) [4]. After use, the filter would be discarded, the RPD frame decontaminated, and rendered ready for use with a new filter.

The complexity of the diverse human face shapes requires a better and more flexible method to design, as described herein, an RPD customized to a user's facial features. The RPD should also facilitate the use of filters with desired filtration efficiencies depending on the degree of protection needed against specific inhalation hazards. The RPD should be reusable to address the supply chain shortages witnessed during the onset of the COVID-19 pandemic. Therefore, the design should facilitate the replacement of the filter and easy decontamination of the RPD frame after each use. By harnessing advanced technologies, including 3D scanning and additive manufacturing, as described herein, for the development of a reusable RPD, the fit experience can be enhanced, and the long-standing issues with today's mass-produced FFRs can be addressed.

Additional Discussion

The protection of healthcare workers in the event of an influenza pandemic is a national imperative, and personal protective equipment (PPE) is at the frontline of defense. The COVID-19 Pandemic has reinforced the importance of personal protective equipment, especially reusable respirators, for healthcare workers on the frontlines [1, 2, 3].

The three key challenges associated with using N95 respirators are the need to "fit" the respirator to the wearer, the annual fit-testing, and reusability. To address these challenges, the concept of scanning an individual's face and creating a customized respirator frame into which a replaceable filter of desired protection level (e.g., N95) has been integrated and developed [4].

Importance of Fit and Continuous Fit Monitoring in Respiratory Protection. The pressure exerted by the respirator on the face at the interface affects both the comfort of the wearer and the leakage at the interface, the face seal. Roberge et al. studied the importance of tethering devices that hold the respirator on the face on repeated doffing and donning [5]. They found "a progressive decline in the loads generated by the top and bottom tethering devices of the three models of N95 FFR tested over the course of multiple simulated donning, doffing, and wear periods in a 2.5-hr span." This change in load (and hence, pressure) on the face seal could alter the "fit" of the respirator leading to leakages and thereby compromising the degree of rated protection from the device. Zhuang et al. (2017) tested 101 different FFRs using 25 subjects [6]. Only 32% of the devices achieved acceptable fit in at least one of three donning for greater than 75% of participants [6]. Studies have shown that the pressure exerted by the tethering devices is inversely proportional to the contact surface areas of the face seal [7].

The pressure exerted by the respirator on the face seal influences the comfort and tolerability of the user. However, there is no "quantitative" metric or indicator upon which the user can depend to know that the device has been donned correctly and that they will be protected while being comfortable. That "sense of security" for healthcare professionals using respirators in the field is a critical factor in enabling them to perform at their best under trying circumstances (e.g., during COVID-19) without being afraid of compromising their personal safety. Furthermore, continuous monitoring of respirator fit is critical for ensuring both the comfort and efficacy of the respirator during use. The ability to "calibrate" the fit (balancing leakage and comfort) with the measured pressure at the face seal will lead to increased compliance with the use of the respirator by healthcare professionals, thus enhancing their protection.

Prevention of Pressure Injuries from Respirators. Continuous monitoring of face seal pressure, a measure of fit, is critical for yet another reason, viz., preventing pressure injuries (ulcers) associated with the long-term use of respirators [8]. A tight-fitting respirator used continuously over long durations appears to cause skin irritation, injury, and pain [9, 10]. In fact, the cost of treating pressure injuries is estimated to be 2.5 times the cost of preventing them [11]. Therefore, fit monitoring data can facilitate "evidencebased" decision-making on the safe use of respirators. Cai et al. (2018) developed a force sensor system that was inserted between the FFR and the headform to measure the pressure at the face seal [12]. However, due to the limitations of the force sensor system, they could measure the contact pressure at only a single point at a time. Consequently, they could not concurrently monitor the fit throughout the face seal in real-time, which is critical to ensure the desired degree of protection for the user at all times [12]. The exemplary system and method can prevent or reduce such injuries by providing customized shaped RPD based on facial taxonomy that can fit on a user's face without stress points or lines.

Although example embodiments of the present disclosure are explained in some instances in detail herein, it is to be understood that other embodiments are contemplated. Accordingly, it is not intended that the present disclosure be limited in its scope to the details of construction and arrangement of components set forth in the following description or illustrated in the drawings. The present disclosure is capable of other embodiments and of being practiced or carried out in various ways.

It must also be noted that, as used in the specification and the appended claims, the singular forms "a," "an," and "the" include plural referents unless the context clearly dictates otherwise. Ranges may be expressed herein as from "about" or "5 approximately" one particular value and/or to "about" or "approximately" another particular value. When such a range is expressed, other exemplary embodiments include the one particular value and/or to the other particular value.

By "comprising" or "containing" or "including" is meant that at least the name compound, element, particle, or method step is present in the composition or article or method, but does not exclude the presence of other compounds, materials, particles, method steps, even if the other such compounds, material, particles, method steps have the same function as what is named.

In describing example embodiments, terminology will be resorted to for the sake of clarity. It is intended that each term contemplates its broadest meaning as understood by those skilled in the art and includes all technical equivalents that operate in a similar manner to accomplish a similar purpose. It is also to be understood that the mention of one or more steps of a method does not preclude the presence of additional method steps or intervening method steps between those steps expressly identified. Steps of a method may be performed in a different order than those described herein without departing from the scope of the present disclosure. Similarly, it is also to be understood that the mention of one or more components in a device or system does not preclude the presence of additional components or intervening components between those components expressly identified.

The term "about," as used herein, means approximately, in the region of, roughly, or around. When the term "about" is used in conjunction with a numerical range, it modifies that range by extending the boundaries above and below the numerical values set forth. In general, the term "about" is used herein to modify a numerical value above and below the stated value by a variance of 10%. In one aspect, the term "about" means plus or minus 10% of the numerical value of the number with which it is being used. Therefore, about 50% means in the range of 45%-55%. Numerical ranges recited herein by endpoints include all numbers and fractions subsumed within that range (e.g., 1 to 5 includes 1, 1.5, 2, 2.75, 3, 3.90, 4, 4.24, and 5).

Similarly, numerical ranges recited herein by endpoints include subranges subsumed within that range (e.g., 1 to 5 includes 1-1.5, 1.5-2, 2-2.75, 2.75-3, 3-3.90, 3.90-4, 4-4.24, 4.24-5, 2-5, 3-5, 1-4, and 2-4). It is also to be understood that all numbers and fractions thereof are presumed to be modified by the term "about."

The following patents, applications, and publications, as listed below and throughout this document, are hereby incorporated by reference in their entirety herein.

REFERENCES

[1] Institute of Medicine. 2008. Preparing for an Influenza Pandemic: Personal Protective Equipment for Healthcare Workers. Washington, DC, https://doi.org/10.17226/11980.

[2] Institute of Medicine. 2006. Reusability of Facemasks During an Influenza Pandemic: Facing the Flu. Washington, DC, https://doi.org/10.17226/11637.

[3] National Academies of Sciences, Engineering, and Medicine. 2019. Reusable Elastomeric Respirators in Health Care: Considerations for Routine and Surge Use. Washington, DC: The National Academies Press. https://doi.org/10.17226/25275.

[4] Jayaraman, S., and Park, S., Respiratory Protection Device, U.S. Pat. No. 10,646,731.

[5] Roberge, R., Niezgoda, G., Benson, S., Analysis of Forces Generated by N95 Filtering Facepiece Respirator Tethering Devices: A Pilot Study, Journal of Occupational and Environmental Hygiene, 9 (8), 2012, pp. 527-533.

[6] Zhuang, Z., Bergman, M., Lei, Z., Niezgoda, G. & Shaffer, R. (2017) Recommended test methods and pass/fail criteria for a respirator fit capability test of half-mask air-purifying respirators. *J. Occup. Environ. Hyg.* 14, 473-481. https://doi.org/10.1080/15459624.2017.1296233.

[7] Yang J, Dai J, Zhuang Z. Simulating the interaction between a respirator and a headform using LS-DYNA. Computer-Aided Design Appl. 2009; 6(4):539-551.

[8] Protecting facial skin under N95 face masks, National Pressure Injury Advisory Panel, https://cdn.ymaws.com/npiap.com/resource/resmgr/position_statements/NPIAP_-Mask_Injury_Infograp.pdf, Last Accessed: Jun. 19, 2020.

[9] Stokowski, L. A. (2020) A Step-by-Step Guide to Preventing PPE-Related Skin Damage. MedScape. Retrieved from https://www.medscape.com/viewarticle/929590.

[10] Lam, U-Nee., Siddik, Nur., Yussof, Shah., and Ibrahim, S. (2020) N95 respirator associated pressure ulcer amongst COVID-19 health care workers, Int Wound J. October; 17(5): 1525-1527, doi: 10.1111/iwj.13398.

[11] Oot-Giromini B, Bidwell F C, Heller N B, et al. Pressure ulcer prevention versus treatment, comparative product cost study. Decubitus 1989; 2(3):52-4.

[12] Cai, M., Li., H., Shen, S., Wang, Y, and Yang, Q. (2018) "Customized design and 3D printing of face seal for an N95 filtering facepiece respirator", Journal of Occupational and Environmental Hygiene, 15:3, 226-234, https://doi.org/10.1080/15459624.2017.1411598

[13] Zhuang, Z., & Bradtmiller, B. (2005) A Head-and-Face Anthropometric Survey of U.S. Respirator Users. *J Occup Environ Hyg.* November; 2 (11):567-76. DOI: https://10.1080/15459620500324727. PMID: 16223715.

[14] 3dMD. (2020) Retrieved from https://3dmd.com/products/.

[15] Granta. (2020) Chart from CES EduPack, *ANSYS Granta.* 2019.

[16] Ashby. (2008) The CES EduPack Database of Natural and Man-Made Materials, Version 1.0, *Granta Design*, Cambridge, UK, January 2008.

[17] Shore. (2020) "Shore hardness scale," https://www.smooth-on.com/page/durometer-shore-hardness-scale/, Last Accessed: Nov. 14, 2020.

[18] Formlabs. (2022a) Elastic 50A, https://formlabs.com/materials/flexible-elastic/. Last Accessed: Jun. 19, 2022.

[19] Carbon 3D. (2022) SIL 30, https://www.carbon3d.com/materials/sil-30, Last Accessed: Jun. 18, 2022.

[20] Dow. (2022) SILASTIC™ 3D 3335 Liquid Silicone Rubber, https://www.dow.com/en-us/pdp.silastic-3-d-3335-liquid-silicone-rubber-lsr.4137603z.html?productCatalogFlag=1#overview, Last Accessed: Jun. 18, 2022

[21] Elkem. (2019) Silicones 3D Flyer Industrial, https://www.elkem.com/silicones/brands/amsil/, Last Accessed: Jun. 18, 2022

[22] Chopra, J., Abiakam, N., and Kim, H. (2021) The influence of gender and ethnicity on facemasks and respiratory protective equipment fit: a systematic review and meta-analysis. BMJ Global Health 6:e005537. doi: 10.1136/bmjgh-2021-005537.

[23] Zhuang, Z., Groce, D., Ahlers, H. W., Iskander, W., Landsittel, D., Guffey, S., Benson, S., Viscusi, D., and Shaffer, R. E. (2008) Correlation between Respirator Fit and Respirator Fit Test Panel Cells by Respirator Size. *Journal of Occupational and Environmental Hygiene,* 5(10), 617-628. https://doi.org/10.1080/15459620802293810

[24] Lin, Y. C., & Chen, C. P. (2017) Characterization of small-to-medium head-and-face dimensions for developing respirator fit test panels and evaluating fit of filtering facepiece respirators with different faceseal design. *PLOS ONE,* 12(11), e0188638. https://doi.org/10.1371/journal.pone.0188638.

[25] NASEM. (2022) *Frameworks for Protecting Workers and the Public from Inhalation Hazards*. Washington, DC: The National Academies Press. https://doi.org/10.17226/26372.

What is claimed includes:

1. A method of fabricating a respiratory protective device, the method comprising:
   acquiring (i) a set of images or scans of a user or (ii) a scanned facial profile of the user;
   generating, by a processor, a model of the facial profile of a facial region of the user based on (i) the set of images or scans of the user or (ii) the scanned facial profile of the user;
   determining, by the processor, (i) a plurality of anatomical facial landmarks, including at least an infraorbitale and a zygomatic, and (ii) a plurality of mathematically determined landmarks derived from the plurality of anatomical facial landmarks, including a face side point, a jaw side point, and a jaw point, wherein the plurality of mathematically determined landmarks are derived by projecting the plurality of anatomical facial landmarks onto 2D planes to determine intermediate process landmarks;
   determining, by the processor executing a taxonomy model, using the determined plurality of anatomical facial landmarks and the plurality of mathematically determined landmarks derived therefrom, at least one of a frame or a contour thereof that can be fit-ably placed on the user that extends over both upper-cheek regions of the user, over both mid-cheek position regions of the user, and a chin region of the user, wherein the frame matches the taxonomy model and has facial landmarks identified on the face of the user in the scanned facial profile,
   wherein the at least one of the frame or the contour thereof is employed in one or more manufacturing operations to manufacture or fabricate the frame having the contour that maintains a breathable filter covering over the facial region of the user.

2. The method of claim 1, wherein the frame includes at least a portion of the contour placed at the plurality of mathematically determined landmarks on the user's facial anatomy, wherein the contour is configured to be over, or in proximity to, at least one of:
   a pronasale facial region, a sellion facial region, or a region therebetween;
   an infraorbitale facial region, a zygomatic facial region, or a region therebetween;
   a chin point facial region, a gonion facial region, or a region therebetween; or
   a menton facial region, a sagittal plane, or a region therebetween.

3. The method of claim 2, wherein the plurality of mathematically determined landmarks include:
   the pronasale facial region, the sellion facial region, or the region therebetween;
   the infraorbitale facial region, the zygomatic facial region, or the region therebetween;
   the chin point facial region, the gonion facial region, or the region therebetween; or
   the menton facial region, the sagittal plane, or the region therebetween.

4. The method of claim 1, wherein the plurality of anatomical facial landmarks, and the plurality of mathematically determined landmarks derived therefrom is determined by a first algorithmic process.

5. The method of claim 1, wherein the at least one of the frame or the contour thereof is determined by an algorithmic process.

6. The method of claim 1, wherein the one or more manufacturing operations comprises injection molding with elastomeric materials.

7. The method of claim 1, further comprising:
   determining, by the processor, fastening hooks on the frame by an algorithmic process.

8. The method of claim 1, the frame comprises a material compatible with a decontaminating operation comprising UV radiation or cleaning solvents.

* * * * *